US012678315B2

(12) United States Patent
Faux et al.

(10) Patent No.: US 12,678,315 B2
(45) Date of Patent: Jul. 14, 2026

(54) ORTHOSIS BRACE COMPRISING REEL-BASED LACING SYSTEM AND FASTENERS FOR RELEASABLY COUPLING THE ORTHOSIS BRACE TO FOOTWEAR

(71) Applicant: FOOTSCIENTIFIC INC., Draper, UT (US)

(72) Inventors: Jonathan Robert Faux, Draper, UT (US); Chris Hughes, Draper, UT (US); Gary Moore, Draper, UT (US)

(73) Assignee: FOOTSCIENTIFIC INC., Draper, UT (US)

( * ) Notice: Subject to any disclaimer, the term of this patent is extended or adjusted under 35 U.S.C. 154(b) by 257 days.

(21) Appl. No.: 18/678,816

(22) Filed: May 30, 2024

(65) Prior Publication Data

US 2024/0390171 A1    Nov. 28, 2024

(51) Int. Cl.
*A61F 5/01* (2006.01)
*A43B 7/20* (2006.01)
(52) U.S. Cl.
CPC .............. *A61F 5/0113* (2013.01); *A43B 7/20* (2013.01)
(58) Field of Classification Search
CPC .... A61F 5/0113; A61F 5/0111; A61F 5/0109; A61F 5/0106; A61F 5/0104; A61F 5/0102; A61F 5/01; A43B 7/20; A43B 7/19; A43B 7/18; A43B 7/00
See application file for complete search history.

(56) References Cited

U.S. PATENT DOCUMENTS

| | | | | |
|---|---|---|---|---|
| 5,445,602 A | * | 8/1995 | Grim ...................... | A61F 5/012 602/6 |
| 8,986,235 B2 | * | 3/2015 | Weaver, II ............ | A61F 5/0111 602/61 |
| 9,427,350 B1 | * | 8/2016 | Clements .................. | A61F 5/01 |
| 9,717,619 B2 | * | 8/2017 | Dodin ................... | A61F 5/0102 |

(Continued)

FOREIGN PATENT DOCUMENTS

| | | | | | |
|---|---|---|---|---|---|
| CA | 3036219 A1 | * | 3/2018 | ............ | A61F 5/0111 |
| CN | 108135330 A | * | 6/2018 | ............... | A43C 1/00 |

(Continued)

OTHER PUBLICATIONS

International Search Report and Written Opinion for International Application No. PCT/US2021/37929, dated Oct. 21, 2021.

*Primary Examiner* — Tarla R Patel
(74) *Attorney, Agent, or Firm* — TechLaw Ventures, PLLC; Terrence J. Edwards

(57) ABSTRACT

Orthosis brace comprising a system for alleviating foot drop experienced by a user. A system includes a first fastener configured to attach to a shoe and a second fastener configured to attach to the shoe. The system includes a support configured to wrap around at least a portion of a lower leg of a user. The system includes a lace support attached to the support, wherein the lace support is configured to receive a lace. The system includes a first shoe connector that is configured to be coupled to the first fastener to releasably couple the support to the shoe when the first fastener is attached to the shoe. The system includes a second shoe connector that is configured to be coupled to the second fastener to releasably couple the support to the shoe when the second fastener is attached to the shoe.

18 Claims, 20 Drawing Sheets

(56)                    References Cited

U.S. PATENT DOCUMENTS

| | | | |
|---|---|---|---|
| 11,690,748 B2 | 7/2023 | Faux | |
| 2011/0082404 A1 | 4/2011 | Wenger | |
| 2012/0004587 A1 * | 1/2012 | Nickel | A61F 5/028 |
| | | | 602/5 |
| 2012/0246974 A1 * | 10/2012 | Hammerslag | A43C 11/004 |
| | | | 36/83 |
| 2014/0276318 A1 * | 9/2014 | Faux | A61F 5/0109 |
| | | | 602/28 |
| 2014/0276320 A1 * | 9/2014 | Faux | A61F 5/0113 |
| | | | 602/28 |
| 2017/0105489 A1 | 4/2017 | Lovett | |
| 2020/0069002 A1 | 3/2020 | Fiedler et al. | |
| 2021/0393428 A1 | 12/2021 | Faux et al. | |

FOREIGN PATENT DOCUMENTS

| | | | | |
|---|---|---|---|---|
| DE | 102018201019 A1 * | 8/2018 | | A41D 13/06 |
| EP | 2783661 A1 * | 10/2014 | | A61F 5/0113 |
| WO | WO-2010117723 A2 * | 10/2010 | | A61F 5/0111 |
| WO | WO-2012003396 A2 * | 1/2012 | | A43C 1/003 |
| WO | WO 2021257901 A1 | 12/2021 | | |

* cited by examiner

ORTHOSIS BRACE COMPRISING REEL-BASED LACING SYSTEM AND FASTENERS FOR RELEASABLY COUPLING THE ORTHOSIS BRACE TO FOOTWEAR

CROSS-REFERENCE TO RELATED APPLICATIONS

This application is a continuation-in-part of co-pending U.S. patent application Ser. No. 18/320,636, filed May 19, 2023, entitled "ORTHOSIS BRACE COMPRISING REEL-BASED LACING SYSTEM," which is a continuation of U.S. patent application Ser. No. 16/905,591, filed Jun. 18, 2020 (now U.S. Pat. No. 11,690,748), which are incorporated herein by reference in their entirety, including but not limited to those portions that specifically appear hereinafter, the incorporation by reference being made with the following exception: In the event that any portion of the above-referenced applications are inconsistent with this application, this application supercedes said portion of said above-referenced applications.

TECHNICAL FIELD

The disclosure relates generally to orthoses systems and devices and particularly relates to orthoses configured for treating and alleviating conditions relating to feet.

BACKGROUND

Foot drop (also referred to as "drop foot") is a condition in which a front part of a person's foot drops involuntarily. Foot drop is caused by various conditions, including weakness of the forefoot, injury to the peroneal nerve, paralysis of muscles in the anterior portion of the lower leg, or a variety of other conditions such as stoke, multiple sclerosis, Charcot-Marie-Tooth disease, and others. Foot drop may be temporary or permanent and can affect one foot or both of an individual's feet.

Foot drop can adversely affect an individual's ability to walk. A person with food drop may drag his or her toes along the ground when walking or lift his or her knee higher than normal when walking to prevent the foot from dragging, resulting in what is commonly referred to as "steppage gait." These complications can decrease the mobility of persons affected by foot drop.

Various orthoses are available for treating foot drop. However, these orthoses known in the art are often difficult to set up and adjust. Many orthoses require specialized or modified shoes. The orthoses known in the art are not convenient because they are complex to put on and adjust, can be exceptionally heavy, and lack flexibility. Therefore, there is a need for adjustable, and easy-to-use orthoses to assist individuals experiencing foot drop.

In light of the foregoing, disclosed herein are systems, methods, and devices for raising a forefoot of a person's foot. Such systems, methods, and devices as disclosed herein can be used to alleviate the conditions associated with foot drop and other conditions that may be addressed by adjusting an angle of the foot relative to the lower leg.

BRIEF DESCRIPTION OF THE DRAWINGS

Non-limiting and non-exhaustive implementations of the present disclosure are described with reference to the following figures, wherein like reference numerals refer to like parts throughout the various views unless otherwise specified. Advantages of the present disclosure will become better understood with regard to the following description and accompanying drawings where:

FIG. 11A is an exploded straight-on side view of an exemplary fastener for releasably coupling an orthosis brace to footwear, such as a shoe;

FIG. 11B is an exploded perspective view of an exemplary fastener for releasably coupling an orthosis brace to footwear, such as a shoe;

FIG. 11C is a perspective view of an exemplary fastener for releasably coupling an orthosis brace to footwear, such as a shoe;

FIG. 12A is an exploded straight-on side view of an exemplary fastener for releasably coupling an orthosis brace to a footwear, such as a shoe;

FIG. 13A is an exploded straight-on side view of an exemplary fastener for releasably coupling an orthosis brace to footwear, such as a shoe;

DETAILED DESCRIPTION

Figure 1:
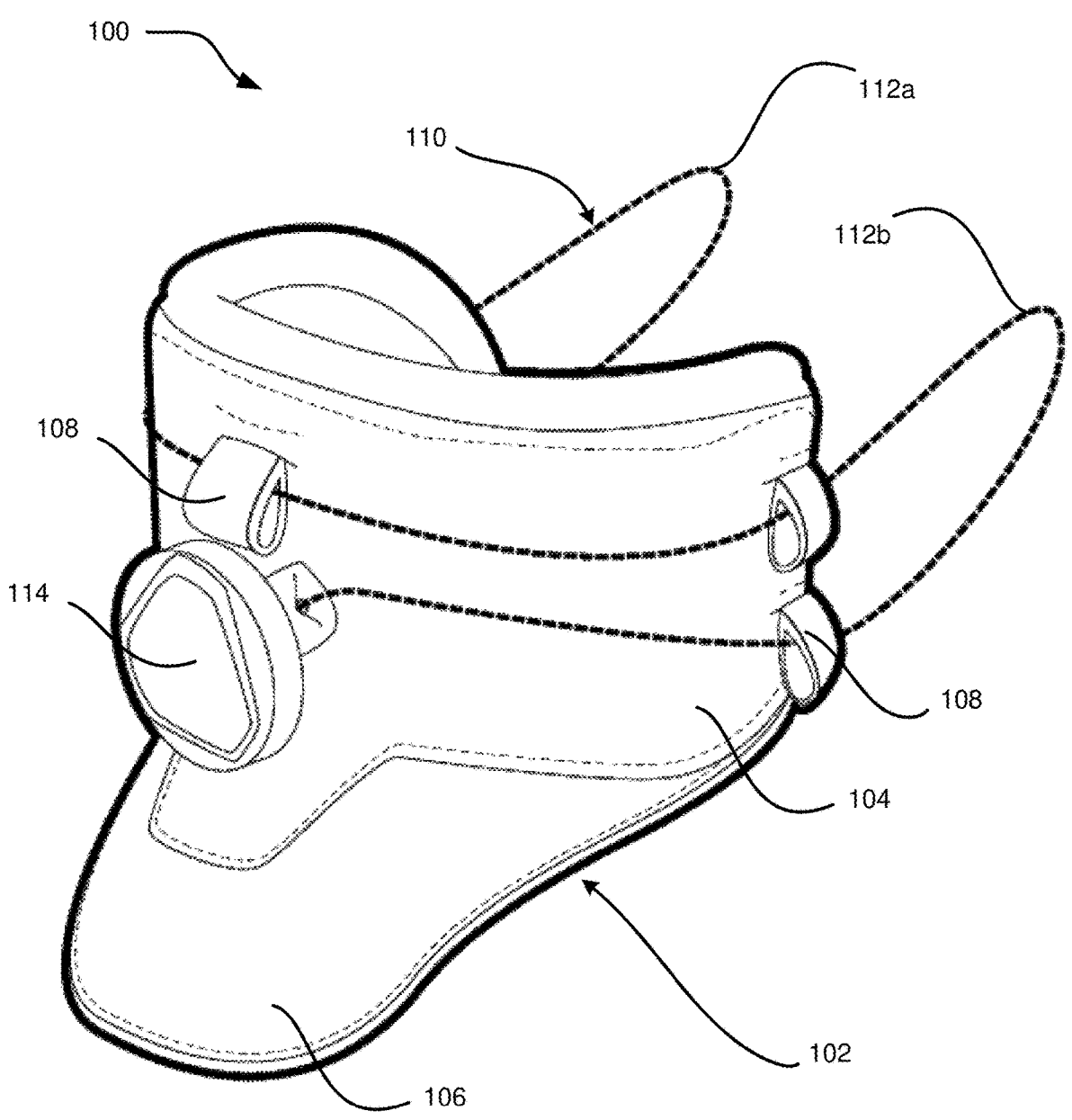
FIG. 1 is a perspective view of an orthosis brace for correcting foot drop and other conditions that may be alleviated by adjusting an angle of the foot relative to the lower leg, according to one embodiment.

Disclosed herein are systems, methods, and devices for alleviating conditions associated with foot drop and other conditions that may be addressed by adjusting an angle of the foot relative to the lower leg. For the sake of simplicity, such an orthosis may be referred to herein as an "orthosis brace." An orthosis brace may be configured to exert an upward force on a foot-receiving member such as an item of footwear or some other foot-receiving member configured to be worn on an individual's foot.

An embodiment of the disclosure is an orthosis brace for addressing foot drop. The orthosis brace includes a support configured to wrap around at least a portion of a lower leg of a user and a lace support attached to the support and configured to receive a lace. The orthosis brace further includes a reel-based fastener attached to the support, wherein the reel-based fastener comprises a reel for receiving the lace and adjusting a tautness of the lace.

Before the structures, systems, and methods for integrating a surveillance system with a digital lockbox are disclosed and described, it is to be understood that this disclosure is not limited to the particular structures, configurations, process steps, and materials disclosed herein as such structures, configurations, process steps, and materials may vary somewhat. It is also to be understood that the terminology employed herein is used for the purpose of describing particular embodiments only and is not intended to be limiting since the scope of the disclosure will be limited only by the appended claims and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element or step not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

As used herein, the terms footwear and shoe may be used interchangeably to refer to any type of outer covering for a user's feet worn by a user and to which an anchor, or other attachment mechanism that may be used in conjunction with a foot brace disclosed herein, may be attached.

Reference will now be made in detail to the exemplary embodiments, examples of which are illustrated in the accompanying drawings. Wherever possible, the same reference numbers are used throughout the drawings to refer to the same or like parts. It is further noted that elements disclosed with respect to embodiments are not restricted to only those embodiments in which they are described. For example, an element described in reference to one embodiment or figure, may be alternatively included in another embodiment or figure regardless of whether or not those elements are shown or described in another embodiment or figure. In other words, elements in the figures may be interchangeable between various embodiments disclosed herein, whether shown or not.

Referring now to the figures, FIG. 1 is a perspective view of an orthosis brace 100 for correcting foot drop and other conditions that may be alleviated by adjusting an angle of the foot relative to the lower leg. The orthosis brace 100 includes a support 102 for encircling the orthosis brace 100 around a lower portion of a user's leg. The support 102 includes an ankle support portion 104 and a counter support portion 106. The orthosis brace 100 further includes lace supports 108 for providing a tab, loop, eyelet, hole, or other opening for receiving a lace and holding the lace in place. The orthosis brace 100 includes a lace 110 comprising a first shoe connector 112*a* and a second shoe connector 112*b*. The orthosis brace 100 includes a reel-based fastener 114 configured for receiving the lace 110 and winding and/or releasing the lace from a reel for tightening and/or loosening the orthosis brace 100.

The support 102 is configured to wrap around a lower portion of a user's leg. In an embodiment, the support 102 wraps around the posterior or dorsal side of the lower portion of the user's leg. In such an embodiment, the support 102 may contact the user's leg at a region where the Achilles tendon is located within the user's leg. The support 102 may be constructed for a rigid, semi-rigid, or flexible material. In an embodiment, the support 102 comprises an inner frame constructed of rigid plastic, metal, or some other rigid material. The support 102 may additionally be covered in a soft material including a foam cushion or padding along with a fabric wrapping. The support 102 may be constructed of a flexible or non-rigid material that wraps around the user's lower leg and forms to the shape of the user's lower leg.

The ankle support portion 104 of the support 102 is configured to wrap around the posterior or dorsal side of the lower portion of the user's leg. When the orthosis brace 100 is in use, the ankle support portion 104 may be located at or near the region of the user's leg that comprises the Achilles tendon. The ankle support portion 104 may comprise a rigid or semi-rigid inner material covered with a lining to provide cushion and support to the user.

The counter support portion 106 of the support 102 is located below the ankle support portion 104 when the orthosis brace 100 is in use on a user's leg. The counter support portion 106 is configured to come in contact with or be located near the counter of footwear, such as a shoe, when the orthosis brace 100 is in use. The counter of a shoe (may also be referred to as a "heel counter") is located at the rear of a shoe and provide support to the wearer's foot. The counter support portion 106 may be configured to press against or rest upon the counter of a shoe. The counter support portion 106 may also be configured to extend outward relative to the ankle support portion 104 to provide clearance for the counter of a shoe. The counter support portion 106 may be constructed of any suitable rigid or semi-rigid material and may be covered with padding or lining to increase comfort for the user.

The lace supports 108 provide a means to secure the laces 110 of the orthosis brace 100. The lace support 108 may be attached to the support 102 and may be constructed of any suitable material. In an embodiment as illustrated in FIG. 1, the lace support 108 may include a loop of fabric or other material configured for receiving the lace 110 therethrough. The lace supports 108 of the orthosis brace 100 may include one or more of a loop, tab, eyelet, hole, tunnel, channel, or other means for receiving a lace 110 and holding the lace 110 in place while still permitting the lace 110 to slide through the lace support 108.

The lace 110 is configured for tightening the orthosis brace 100 and providing a means for attaching the orthosis brace 100 to a shoe or other device. The lace 110 may comprise any suitable lacing device that may be used with footwear or orthoses. In an embodiment, the lace 110 is constructed of twine or line that can withstand relatively high tension forces. In an embodiment, the lace 110 is constructed of a line such as fishing line and may be constructed from one or more fibers. The one or more fibers of the line may be made of nylon, polyvinylidene fluoride, polyethylene, and others. In an embodiment, the lace 110 is configured for being received by the reel-based fastener 114 and winding in and out of the reel-based fastener 114.

Figure 3:
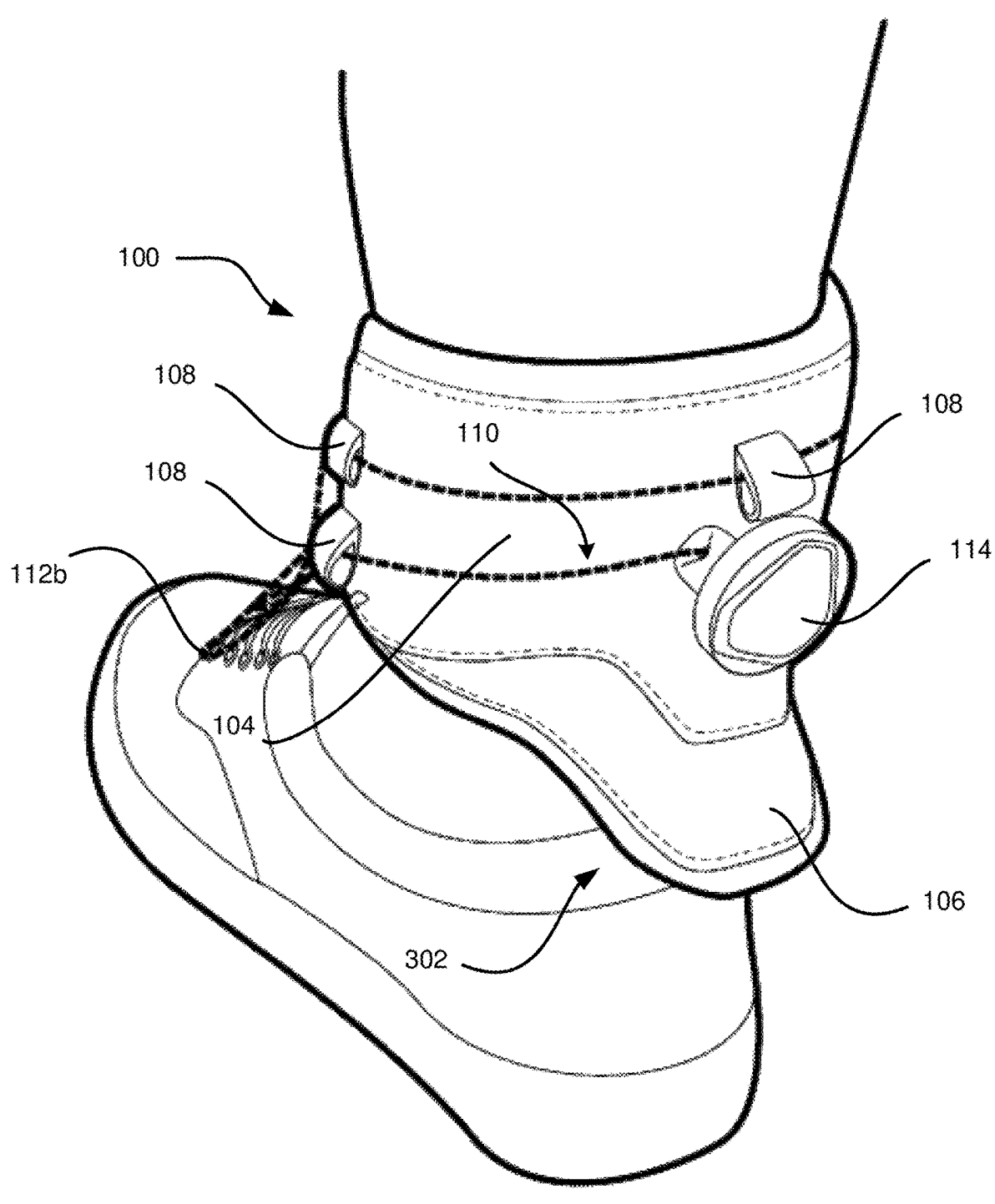
FIG. 3 is a top, rear perspective view of an orthosis brace in use by a user and attached to the user's lower leg, according to one embodiment.
Figure 4:
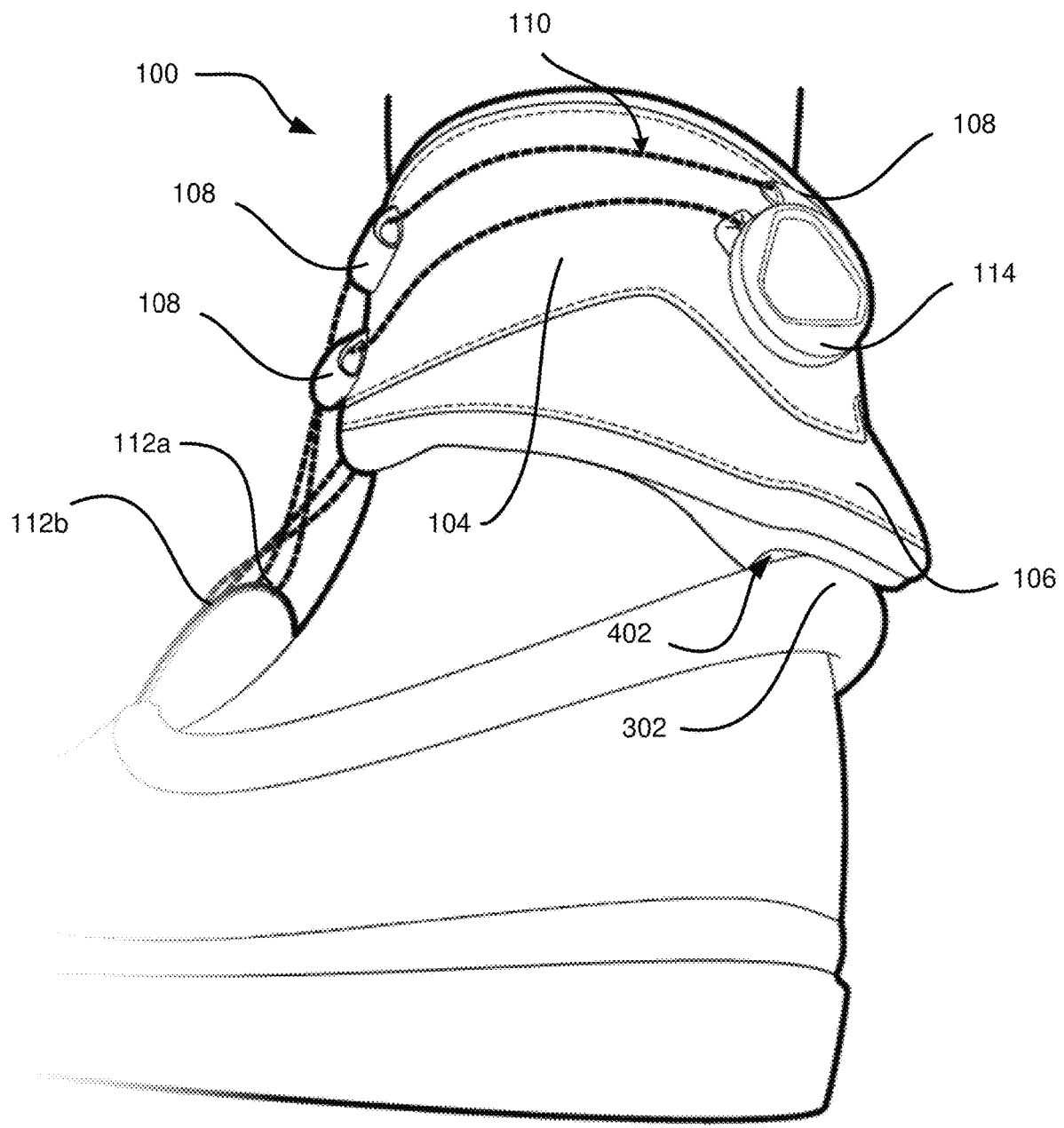
FIG. 4 is a bottom, rear perspective view of an orthosis brace in use by a user and attached to the user's lower leg, according to one embodiment.

The lace 110 includes a first shoe connector 112a and a second shoe connector 112b (may collectively be referred to as shoe connectors 112). The shoe connectors 112 are configured to attach the orthosis brace 100 to a shoe or other footwear. The shoe connectors 112 may comprise a loop in the lace 110 as illustrated in FIG. 1. In alternative embodiments, the shoe connectors 112 may include a fastening element attached to the lace 110 such as a snap, knot, hook, button, latch, and so forth. The shoe connectors 112 provide a means to removably attach the orthosis brace 100 to a shoe or other footwear being worn by a user. In an embodiment, the shoe connectors 112 comprise a loop in the lace 110 configured to be looped around a lace, eyelet, button, or other device of the user's footwear. FIGS. 3-4 illustrate an implementation wherein the orthosis brace 100 is attached to a user's footwear.

The reel-based fastener 114 provides a means to quickly tighten or release the lace 110. In an embodiment, the reel-based fastener 114 comprising a lacing system such as the BOA® Fit System manufactured by BOA®. The reel-based fastener 114 may comprise any suitable lace tightening and loosening system. The reel-based fastener 114 is configured to receive the lace 110 and tighten the tautness of the lace 110 by winding the lace 110 around an internal reel. The reel-based fastener 114 is additionally configured to release the lace 110 and loosen the tautness of the lace 110 by permitting the lace 110 to unwind from the internal reel.

The reel-based fastener 114 may be turned manually by a user to quickly tighten or release the lace 110. The reel-based fastener 114 is configured to securely maintain the tautness of the lace 110 when the position of the internal reel has been set.

In an embodiment, the reel-based fastener 114 comprises a locking mechanism for locking the reel and preventing the lace 110 from unwinding from the reel. In an embodiment, the locking mechanism may be engaged by a user by depressing an exterior housing for the reel-based fastener. In the embodiment, the user may similarly disengage the lock by pulling out the exterior housing. In an embodiment, the user may rotate the reel-based fastener to increase or decrease the tautness of the lace 110 only when the locking mechanism is disengaged.

In an embodiment, the reel-based fastener 114 is configured to maintain the tautness of the lace 110 when the support 102 is wrapped around the lower leg of the user and one or more of the first shoe connector 112a or the second shoe connector 112b is secured to a shoe worn by the user. When the device 100 is in use and secured to the user's shoe, the reel-based fastener 114 can increase, decrease, or maintain the tautness of the lace 110. In an embodiment, a user may decrease the tautness of the lace 110 by turning the exterior housing the reel-based fastener 114 in a counter-clockwise direction and thereby unwinding the reel. In an embodiment, the user may increase the tautness of the lace 110 by turning the exterior housing of the reel-based fastener in a clockwise direction and thereby winding the reel.

Figure 2:
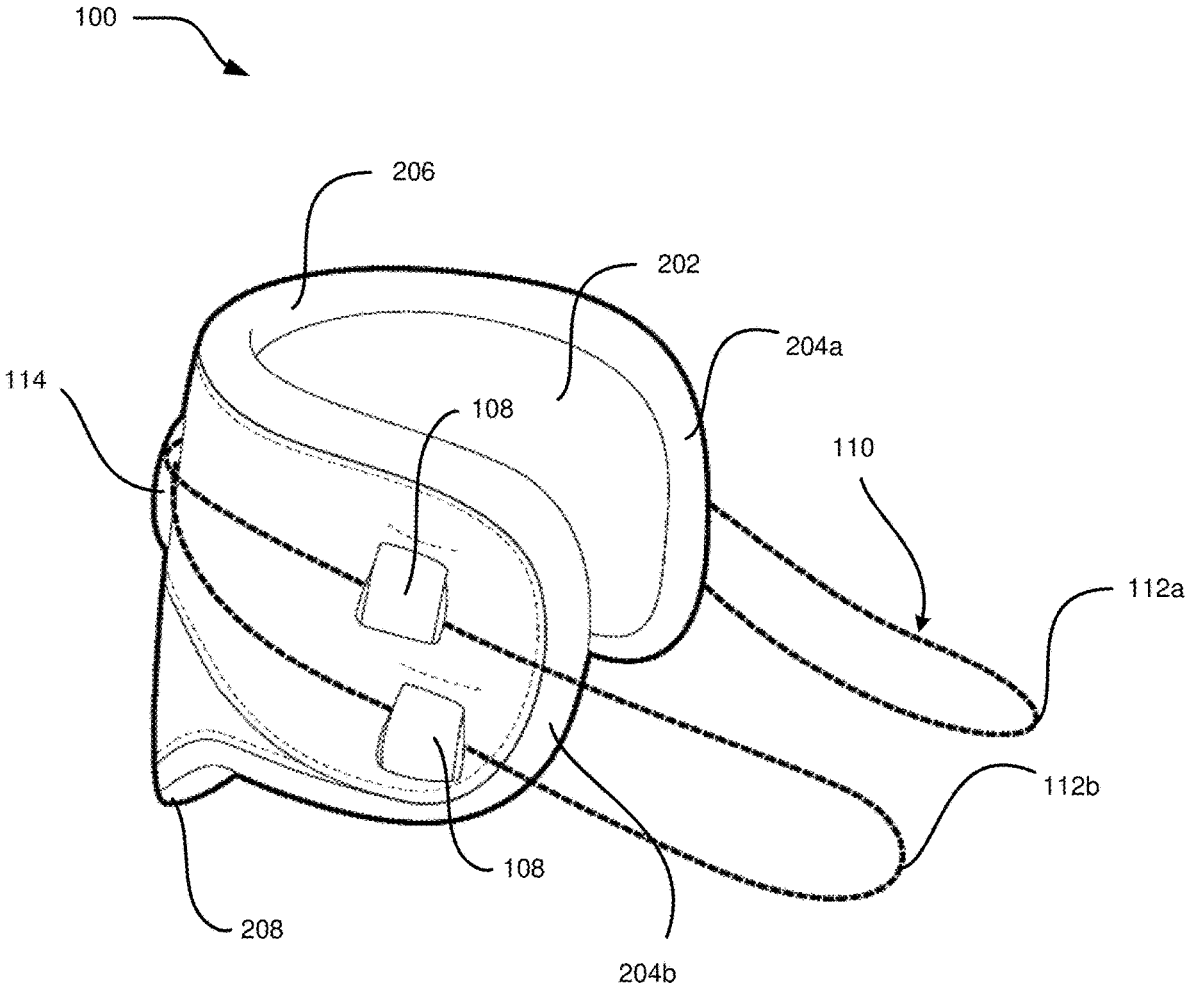
FIG. 2 is a side perspective view of an orthosis brace for correcting foot drop and other conditions that may be alleviated by adjusting an angle of the foot relative to the lower leg, according to one embodiment.

FIG. 2 is a perspective side view of the orthosis brace 100. As illustrated in FIG. 2, the lace 110 may wind through the reel-based fastener 114 at a rear portion of the orthosis brace 100, relative to the anterior side of a user's body when being worn by the user. The lace 110 may then wrap around the sides of the orthosis brace 100 and terminate with loops forming the shoe connectors 112 at the front of the orthosis brace 100, relative to the anterior side of the user's body when being worn by the user.

In an embodiment, the orthosis brace 100 includes inner padding 202 located on an interior side of the orthosis brace 100, relative to the lace 110 on the exterior side of the orthosis brace 100. The inner padding 202 may provide support and comfort to a user when the orthosis brace 100 is securely wrapped around a user's ankle. The inner padding 202 may additionally provide support to reduce the risk the user will experience friction or abrasions that could harm the user's skin when the orthosis brace 100 is being worn.

In an embodiment, the support 102 includes a first support edge 204a and a second support edge 204b (may collectively be referred to herein as the support edges 204). The support 102 further includes an upper edge 206 and a bottom edge 208. The upper edge 206 may constitute the highest point of the device 100 when the device 100 is in use and installed on a user's lower leg. The lower edge 208 may constitute the lowest point of the device 100 and may be configured to rest on or brace against a counter of the user's footwear. In an embodiment, if the support 102 were to be laid out flat, then one side of the support 102 would constitute the first support edge 204a and the opposite side of the support 102 would constitute the second support edge 204b. Further, one long side of the support 102 would constitute the upper edge 206 and the opposite side of the support 102 would constitute the lower edge 208.

The upper edge 206 and the lower edge 208 may comprise a shape and curvature approximately matching the shape and curvature of the user's lower leg. The first support edge 204a and the second support edge 204b may terminate at the anterior side of the user's lower leg when the device 100 is installed on the user's leg and the support 102 is wrapped around the ankle portion of the user's leg. In an embodiment, the first support edge 204a and the second support edge 204b do not touch to complete an elliptical shape. Instead, the first support edge 204a and the second support edge 204b may be located at some point on the anterior side of the user's lower leg and provide an open space on the anterior side of the user's lower leg where the device 100 is not touching the user's leg. This can be beneficial to the user to provide the user with additional space and flexibility for altering the angle of the user's lower leg relative to the user's foot when walking, standing, or moving the foot.

FIG. 3 illustrates a perspective rear view of the orthosis brace 100 when being worn by a user. As shown in FIG. 3, the orthosis brace 100 may be secured to a shoe with the shoe connector 112b. In an embodiment, the shoe connectors 112 cross across the front of the user's footwear to wrap the orthosis brace 100 more securely around the user's ankle. In an alternative embodiment, the shoe connectors 112 do not cross over the front of the user's footwear and instead connect directly outward relative to the orthosis brace 100. Further as illustrated, the orthosis brace 100 may wrap around the user's lower leg such that the counter support portion 106 is located near the counter 302 of the user's footwear. Additionally, the ankle support portion 104 wraps around the posterior side of the user's ankle near the user's Achilles tendon.

In an embodiment, the counter support portion 106 contacts and presses against the counter 302 of the user's footwear. In such an embodiment, the counter 302 of the user's footwear acts as a limiting factor against downward drift of the orthosis brace 100. The counter 302 of the user's footwear, along with the counter support portion 106 of the orthosis brace 100, prevents the orthosis brace 100 from sliding down the user's leg. In an embodiment, the counter support portion 106 includes a thick padding, brace, or other structure configured to press against the counter 302 of the user's footwear (see the footwear counter brace 402 first illustrated in FIG. 4).

The orthosis brace 100 wraps around the posterior side of the user's lower leg and further attaches to the user's footwear. The tautness of the orthosis brace 100 may be altered by winding the reel-based fastener 114 to tighten or release the lace 110. The orthosis brace 100 leverages the support of the user's lower leg along with the support of the user's footwear to lift the user's foot. The orthosis brace 100 thereby alleviates symptoms of foot drop that may be experienced by the user. The user may adjust the degree to which the orthosis brace 100 lifts the user's foot by altering the tautness of the lace 110 by winding the reel-based fastener 114.

FIG. 4 illustrates a perspective underside view of the orthosis brace 100 being worn by a user. FIG. 4 illustrates an embodiment wherein the counter support portion 106 of the support 102 includes a footwear counter brace 402. The footwear counter brace 402 may comprise a channel, cutout, notch, or curvature configured to match the curvature of the counter 302 of the user's footwear. The footwear counter brace 402 is configured to brace against the counter 302 of the user's footwear to support the orthosis brace 100 and further to increase the comfort of wearing the orthosis brace 100 for the user. The footwear counter brace 402 may be specifically shaped and sized for certain types of footwear, for example, for athletic footwear, for specialty orthotic footwear, for leisure footwear, and so forth. In an embodiment, the footwear counter brace 402 is personalized to the user's selected footwear. In an embodiment, the footwear counter brace 402 is adjustable such that it can be used with different types of footwear. In an embodiment, the footwear counter brace 402 is constructed of a semi-rigid foam or padded material configured to press against the counter 302 of the user's footwear. In an embodiment, the footwear counter brace 402 comprises a rigid frame constructed of metal, polycarbonate, wood, or some other rigid material. The footwear counter brace 402 may press against the counter 302 of the user's footwear such that the user's footwear acts as a limiting factor to prevent the orthosis brace 100 from sliding down the user's leg.

Figure 5:
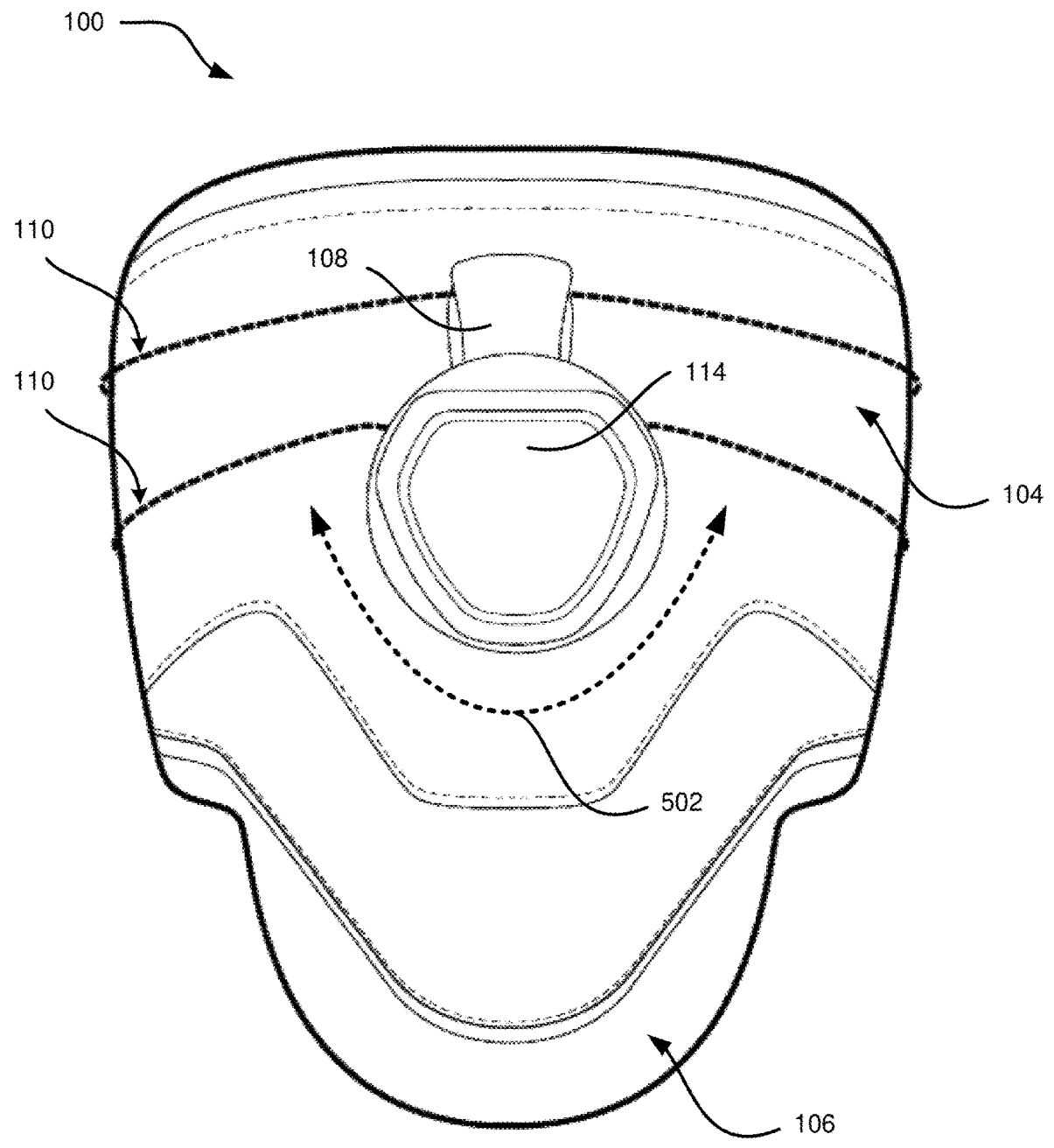
FIG. 5 is a back view of an orthosis brace for correcting foot drop and other conditions that may be alleviated by adjusting an angle of the foot relative to the lower leg, according to one embodiment.

FIG. 5 illustrates a back view of the orthosis brace 100, wherein the rear side of the orthosis brace is the side located at the posterior side of a user's body when the orthosis brace 100 is in use. FIG. 5 further illustrates a straight-on view of the reel-based fastener 114 that may be secured to the back side of the orthosis brace 100. The dotted line 502 indicates that the reel-based fastener 114 may be turned clockwise or counter-clockwise to alter the tautness of the lace 110 wound within the reel-based fastener 114. In an embodiment, a user may turn the reel-based fastener 114 clockwise to wind the lace 110 within the reel-based fastener 114 and thereby tighten the orthosis brace 100. In an embodiment, the user may additionally turn the reel-based fastener 114 counter-clockwise to unwind the lace 110 within the reel-based fastener 114 and thereby loosen the orthosis brace 100. The opposite may be true, and it should be appreciated that the reel-based fastener 114 may be configured to wind and unwind the lace 110 based on either suitable turning direction.

Figure 6:
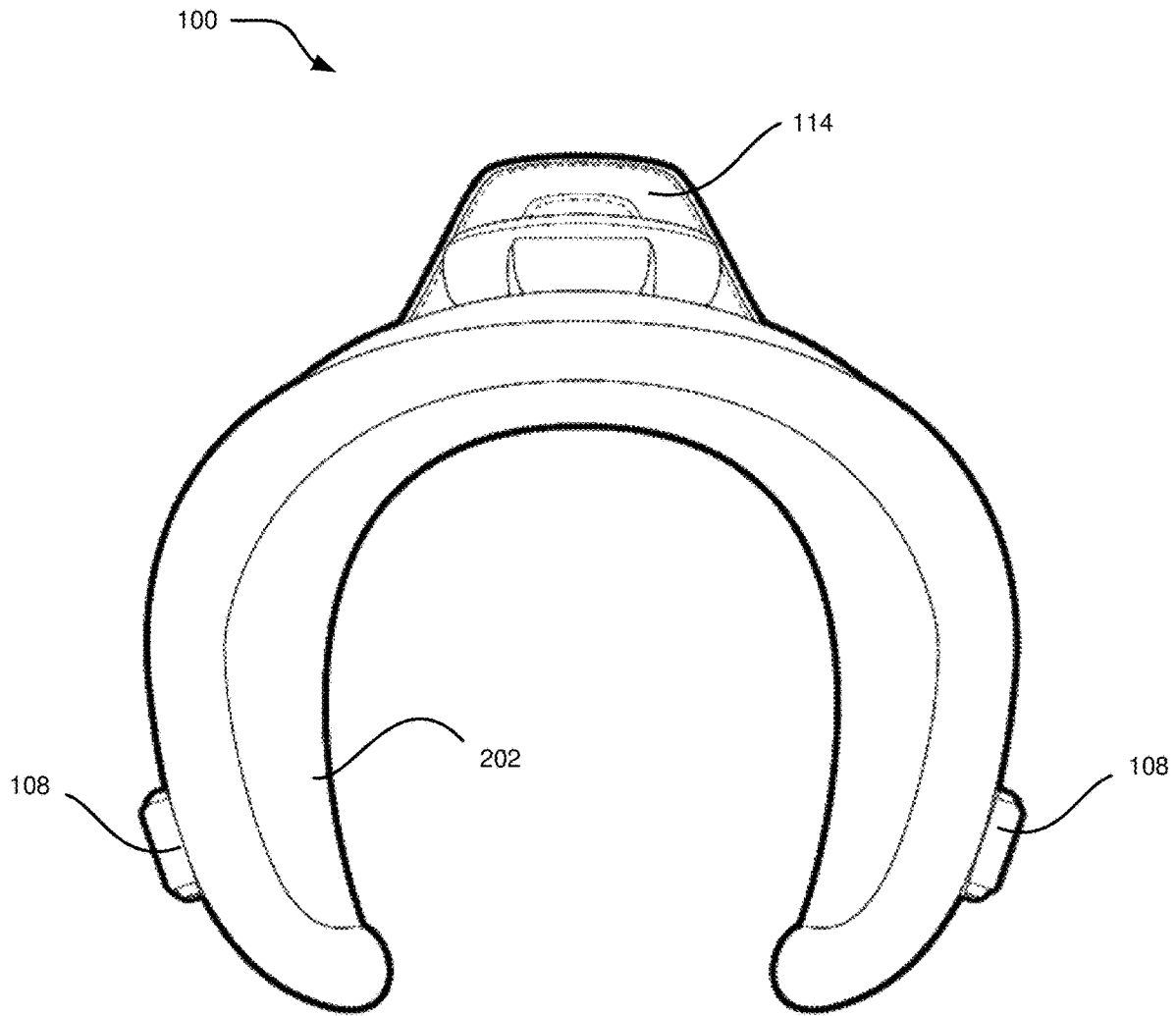
FIG. 6 is an aerial top-down view of an orthosis brace for correcting foot drop and other conditions that may be alleviated by adjusting an angle of the foot relative to the lower leg, according to one embodiment.
Figure 7:
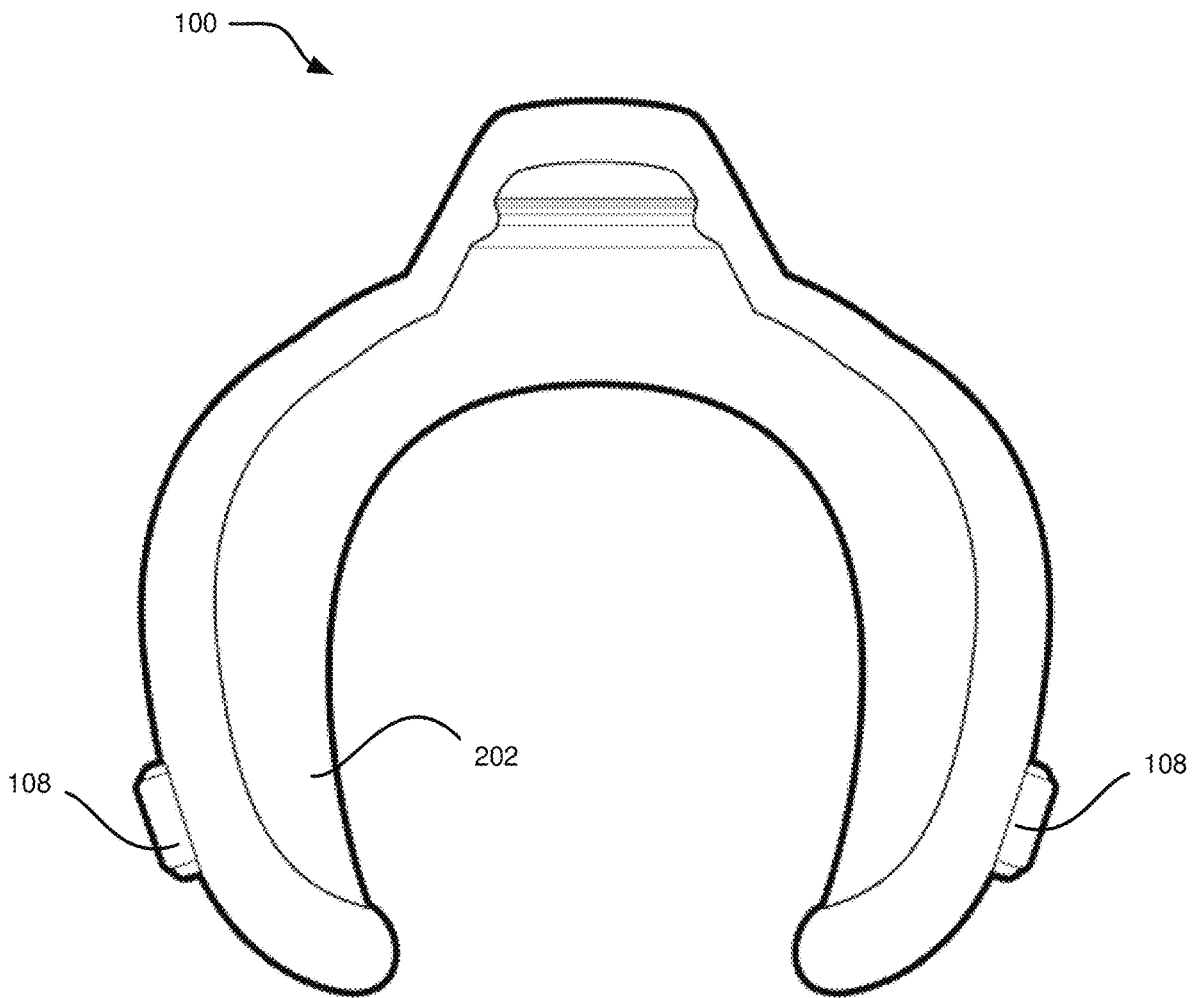
FIG. 7 is an underside view of an orthosis brace for correcting foot drop and other conditions that may be alleviated by adjusting an angle of the foot relative to the lower leg, according to one embodiment.

FIG. 6 illustrates an aerial top-down view of the orthosis brace 100 and FIG. 7 illustrates an underside view of the orthosis brace 100. As shown, the orthosis brace 100 may comprise a curvature configured for wrapping around a user's lower leg. This curvature may be permanently or semi-permanently formed by a rigid, semi-rigid, or semi-malleable material. In an example embodiment, the support 102 comprises a semi-rigid inner material that can be shaped around the user's lower leg and then maintains that shape unless forcibly reformed into a new shape. In an alternative example embodiment, the support 102 comprises a rigid inner material that is irreversibly shaped to the user's lower leg. The orthosis brace 100 may be personalized to a certain user or may be performed to work with all users, or with all users with certain ranges of leg sizes. For example, the orthosis brace 100 may be constructed in "small," "medium," and "large" sizes, as needed, to accommodate different users.

Figure 8:
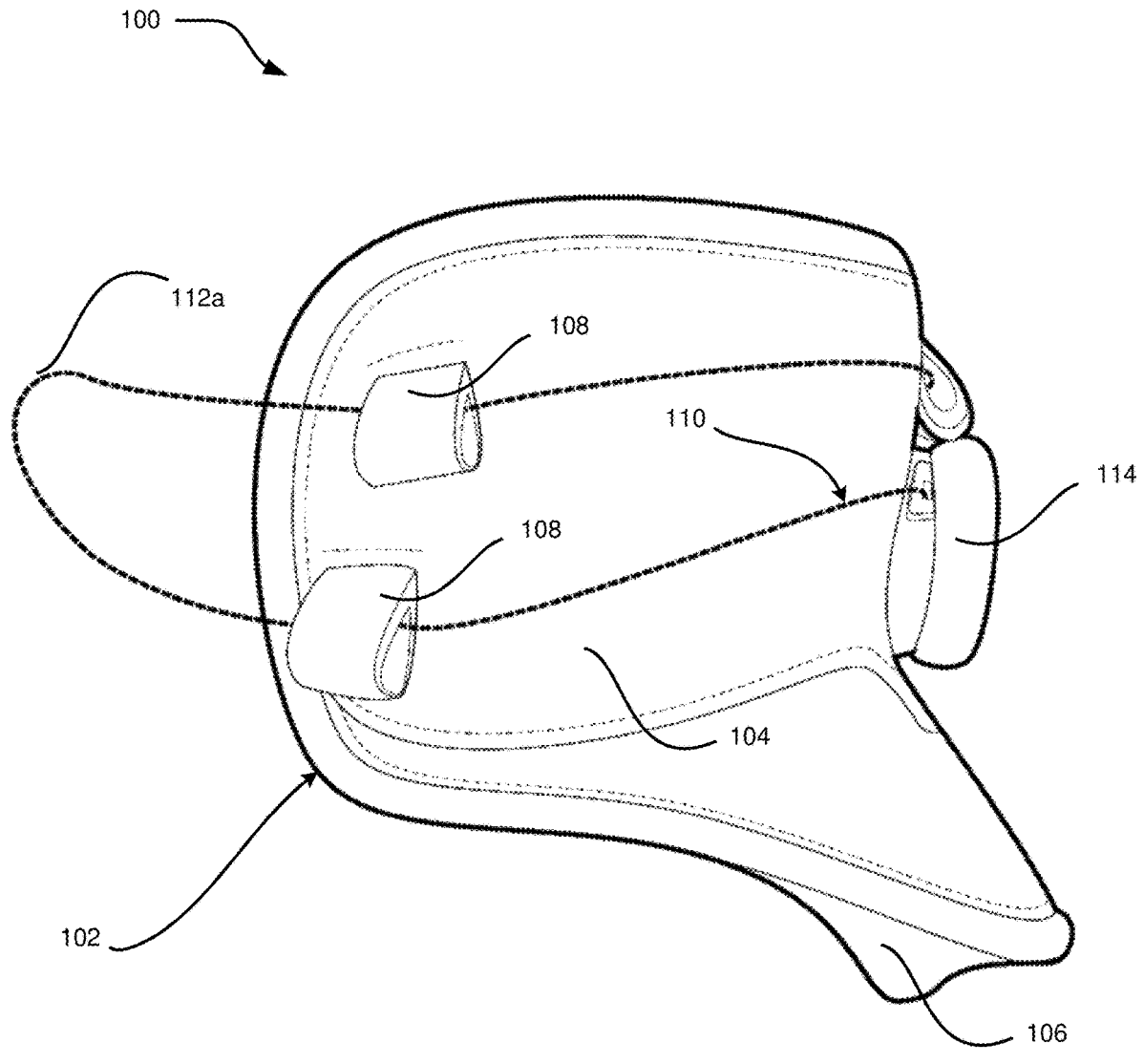
FIG. 8 is a perspective side view of an orthosis brace for correcting foot drop and other conditions that may be alleviated by adjusting an angle of the foot relative to the lower leg, according to one embodiment.
Figure 9:
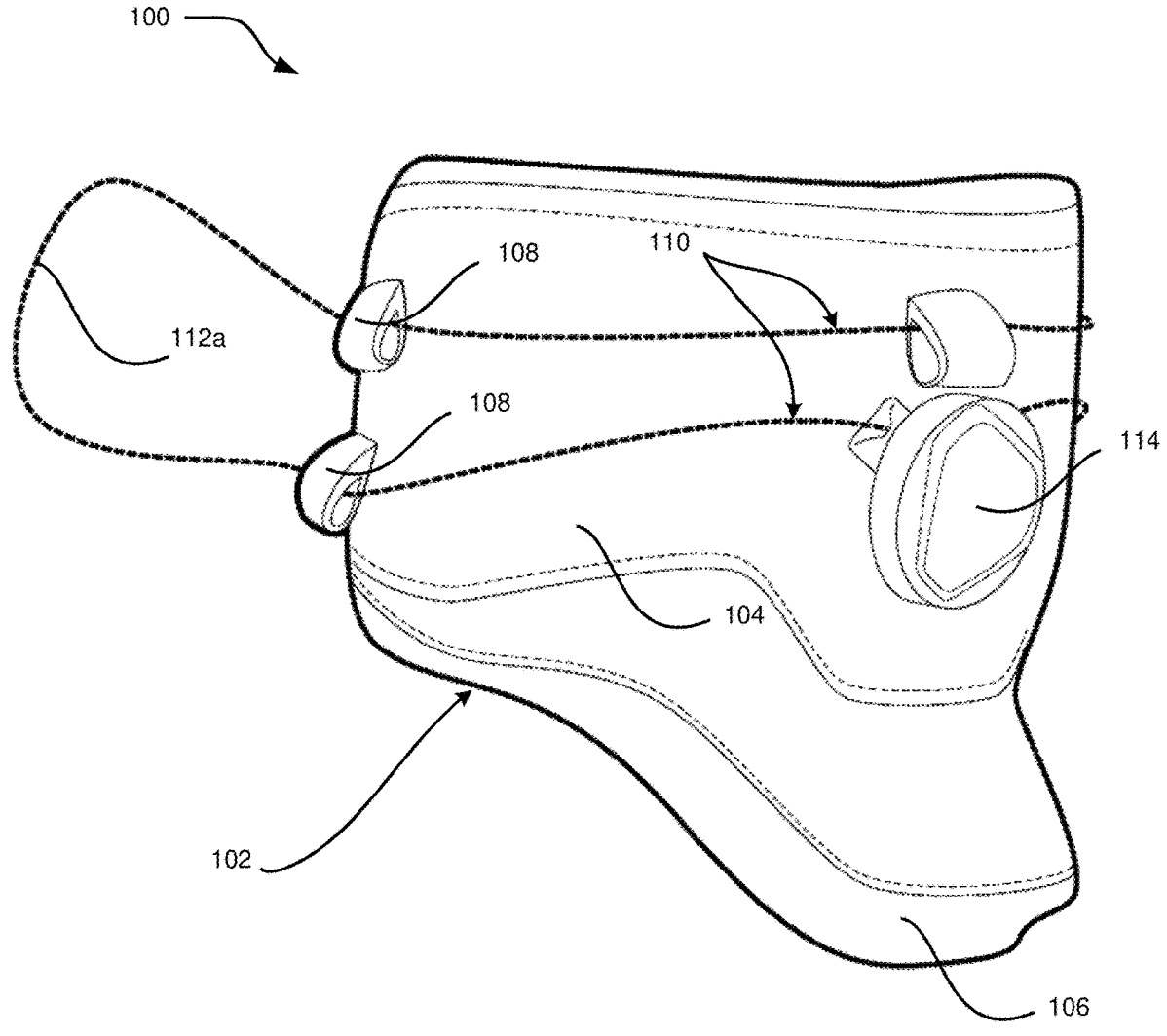
FIG. 9 is a perspective side-back view of an orthosis brace for correcting foot drop and other conditions that may be alleviated by adjusting an angle of the foot relative to the lower leg, according to one embodiment.

FIGS. 8 and 9 illustrate a perspective side views of the orthosis brace 100. As shown, in an embodiment, the lace 110 comprises a single string or twine the terminates inside the reel-based fastener 114. The reel-based fastener 114 secures each of the two ends of the single lace 110 such that the lace 110 forms a continuous loop around the orthosis brace 100. In an embodiment, a first end of the lace 110 is attached to the reel-based fastener and is then fed through two or more lace supports 108 to form the first shoe connector 112. The lace 110 is again fed through two more lace supports 108 on the opposite side of the orthosis brace 100, and then terminates within the reel-based fastener 114. In this embodiment, the tightness of the orthosis brace 100 can quickly be altered by winding or unwinding the reel-based fastener 114.

Figure 10A:
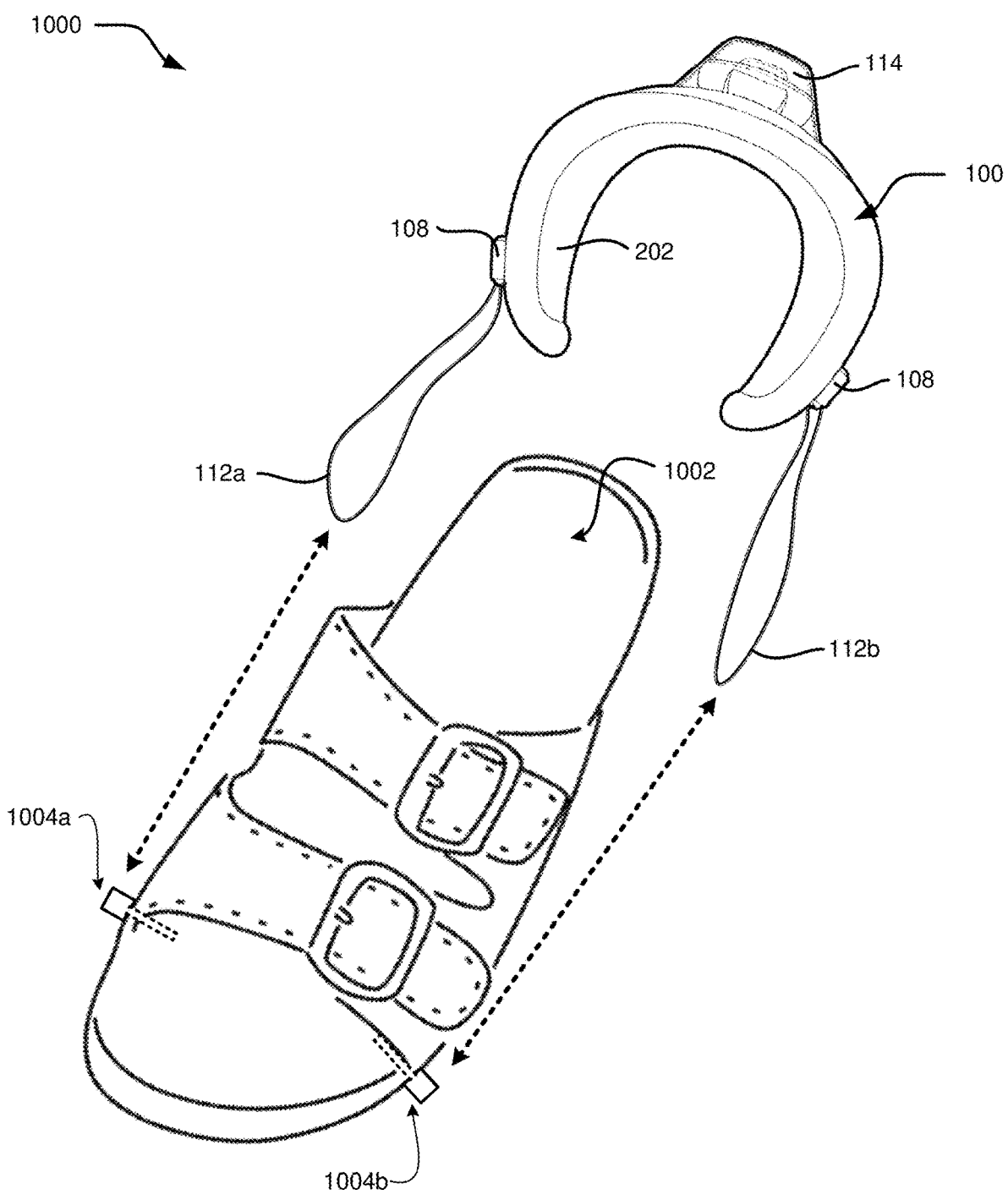
FIG. 10A is a perspective view of a system for releasably coupling an orthosis brace to footwear, such as a shoe, by installing two or more fasteners into the shoe and coupling the orthosis brace to the two or more fasteners, and specifically illustrates wherein the shoe is not coupled to the orthosis brace.
Figure 10B:
FIG. 10B is a perspective view of a system for releasably coupling an orthosis brace to footwear, such as a shoe, by installing two or more fasteners into the shoe and coupling the orthosis brace to the two or more fasteners, and specifically illustrates wherein the shoe is coupled to the orthosis brace.

FIGS. 10A and 10B each illustrate a system 1000 for securing an orthosis brace 100 to a sandal or other shoe that does not include laces like the shoes illustrated in FIGS. 3-4.

FIG. 10A illustrates wherein the orthosis brace 100 is not yet secured to the shoe. FIG. 10B illustrates wherein the orthosis brace 100 is secured to the shoe.

The orthosis brace 100 may secured to any shoe type, including, for example, sandals, heels, loafers, boots, flats, slippers, mules, climbing shoes, flip flops, espadrilles, monk shoes, sneakers, and so forth. The orthosis brace 100 may be secured to shoes with laces according to the example illustrated in FIGS. 3 and 4. The orthosis brace 100 may additionally be secured to shoes without laces according to the system 1000 illustrated in FIGS. 10A-10B, wherein fasteners 1004 are secured to the shoe itself.

The system 1000 includes a shoe 1002 and the orthosis brace 100 secured to the shoe 1002. In the example illustrated in FIGS. 10A-10B, the shoe 1002 is a sandal, but it should be appreciated that the shoe 1002 and the term "shoe" as used herein may include any shoe that includes laces or any shoe that does not include laces. Alternatively, the term shoe may include a shoe that does include laces if the user does not with to connect the orthosis brace 100 to the laces of the shoe. The system 100 includes a first fastener 1004a and a second fastener 1004b that are secured to a sole of the shoe 1002 or another portion of the shoe 1002. The first shoe connector 112a of the orthosis brace 100 connects to the first fastener 1004a that is attached to the shoe 1002. The second shoe connector 112b of the orthosis brace 100 connects to the second fastener 1004b that is attached to the sandal 1002.

In the example illustrated in FIGS. 10A-10B, the first fastener 1004a is attached to the shoe 1002 at a medial side of the shoe 1002. The second fastener 1004b is attached to the shoe 1002 at a lateral side of the shoe 1002. Each of the fasteners 1004a, 1004b is attached to the shoe 1002 near an anterior (i.e., front, nearest the toes) side of the shoe 1002. When the orthosis brace 100 is secured to the shoe 1002, the first shoe connector 112a will run along a medial side of the shoe 1002 and loop around the first fastener 1004a. The second shoe connector 112b will run along a lateral side of the shoe 1002 and loop around the second fastener 1004b.

The fasteners 1004a, 1004b may be identical to one another and installed in different places in the shoe. The fasteners 1004a, 1004b may be different from one another and optimized for placement in a medial or lateral side of the shoe 1002. The fasteners 1004a, 1004b may include any suitable fastener that enables a loop of the shoe connectors 112a, 112b to removably secure to the fasteners 1004a, 1004b. The fasteners 1004a, 1004b may include, for example, a screw with a head, a knob, a hook, a loop, a knot, a bolt, a ring, a carabiner, and so forth. It should be appreciated that the fasteners 1004a, 1004b may include any suitable fastener that enables a user to secure the orthosis brace 100 to the shoe 1002.

Figure 11A:
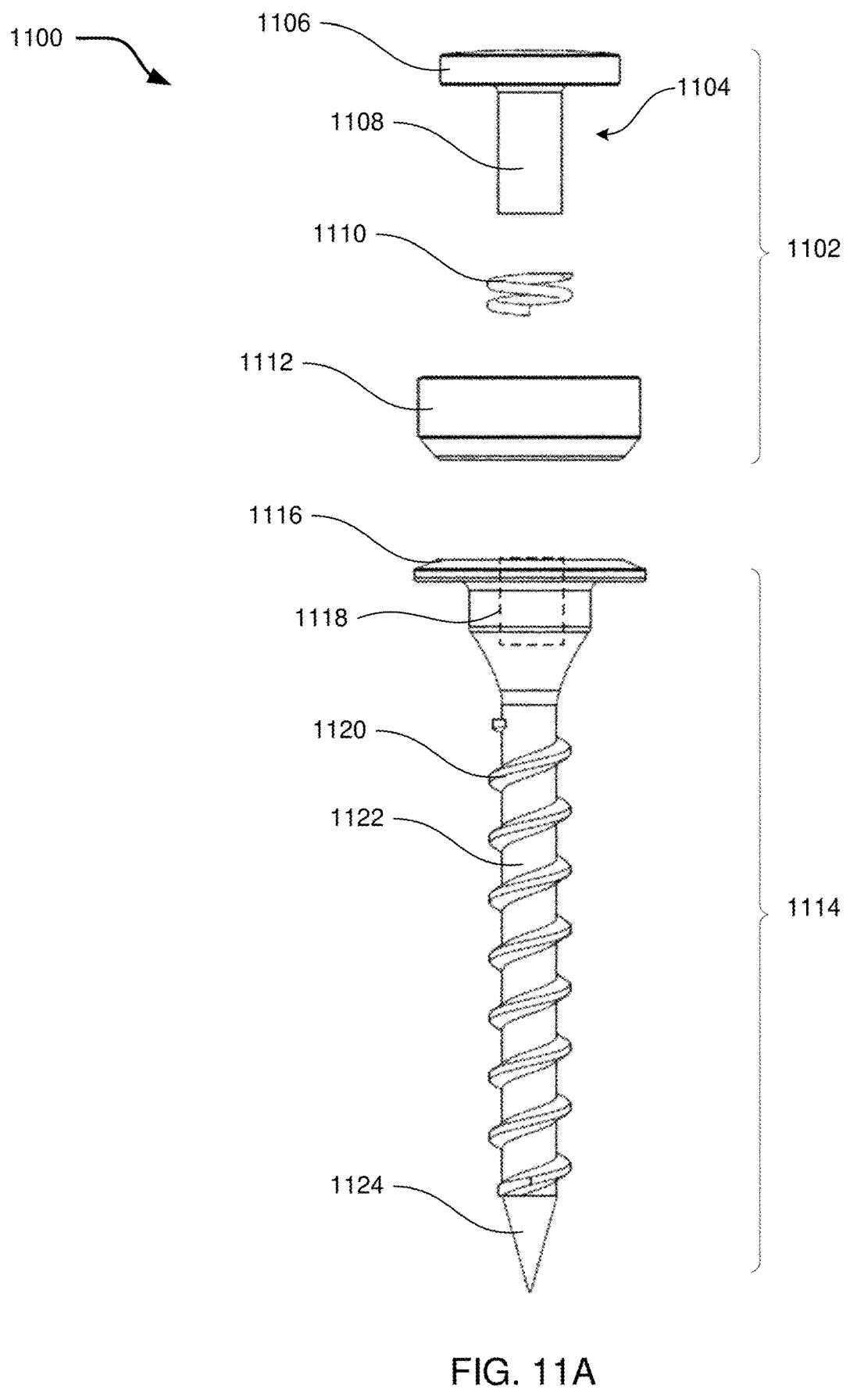
Figures 11B, 11C:
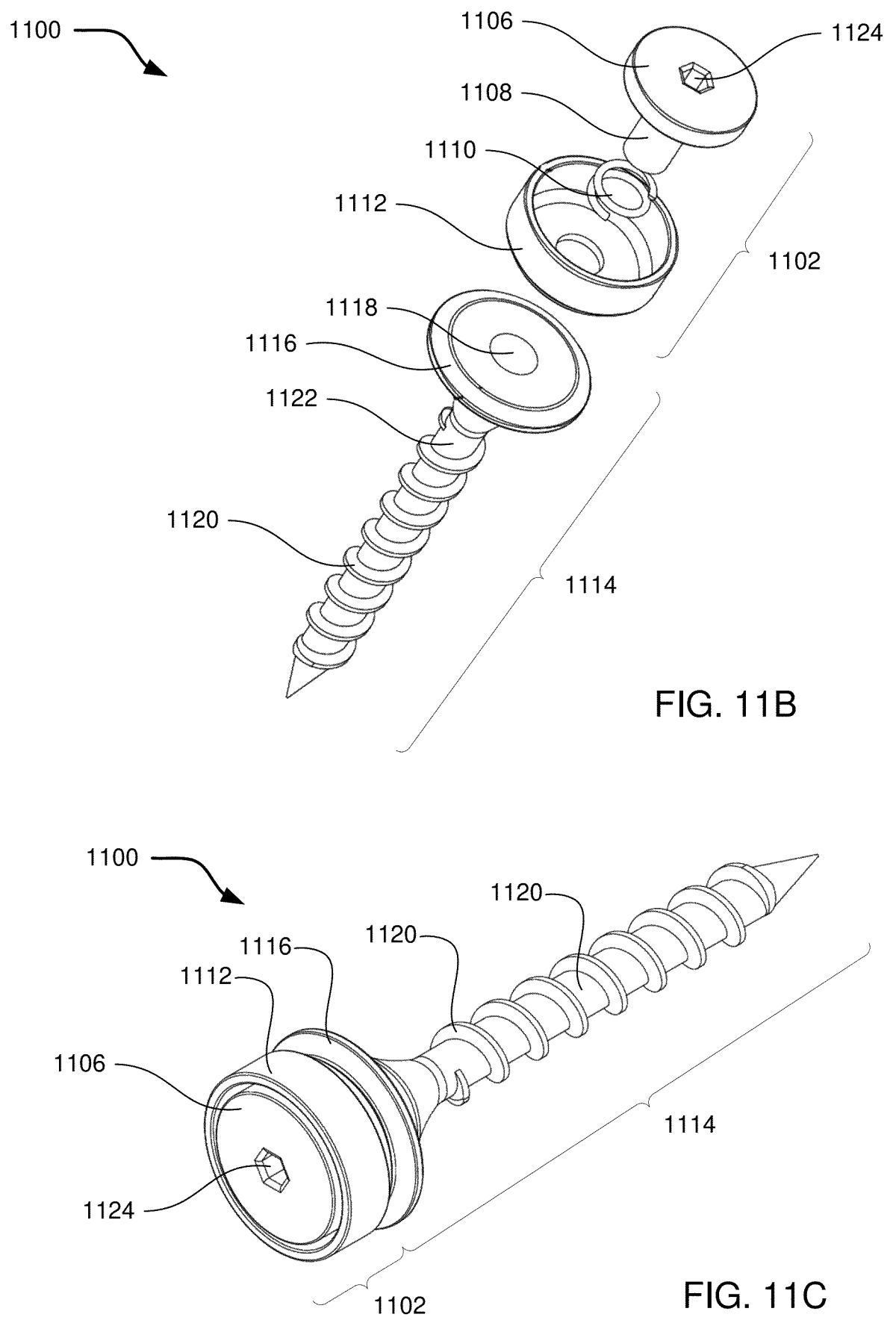

FIGS. 11A-11C illustrate an example fastener 1100 that may be utilized in connection with the system 1000 illustrated in FIGS. 10A-10B. As described herein, the fastener (see 1004a, 1004b at FIGS. 10A-10B) may optionally include a screw or screw assembly as shown in FIGS. 11A-11C. The fastener 1100 illustrated in FIGS. 11A-11C is optimized for insertion into a portion of a shoe and is further optimized to provide a secure head for removably securing the fastener 1100 to the shoe connectors (see 112a, 112b). FIG. 11A is an exploded straight-on side view of components of the fastener 1100. FIG. 11B is an exploded perspective view of components of the fastener 1100. FIG. 11C is an assembled perspective view of the fastener 1100.

The fastener 1100 includes a spring-loaded screw assembly 1102. The spring-loaded screw assembly 1102 includes a screw 1104, which includes a screw head 1106 and a screw body 1108. The spring-loaded screw assembly 1102 further includes a spring 1110 and a retainer 1112, and the spring 1110 is disposed between the retainer 1112 and the screw head 1106. When the components are assembled, the spring 1110 is disposed around the screw body 1108, and the screw body 1108 is disposed within a hollow interior defined by the retainer 1112. Thus, the spring 1110 and screw body 1108 are disposed within the retainer 1112, and the spring 1110 rests on an interior shoulder of the retainer 1112.

The fastener 1100 further includes a mounting screw 1114. The mounting screw 1114 is configured to be attached to the shoe itself (see, e.g., shoe 1002 at FIGS. 10A-10B). The mounting screw 1114 may be threaded into a sole of the shoe near the toe region of the shoe. The mounting screw 1114 includes a head 1116 and a cavity 1118 cut into the head 1116. The cavity 1118 of the mounting screw 1114 is configured to accept the screw body 1108 of the spring-loaded screw assembly 1102. The mounting screw 1114 further includes a body 1122 that includes threading 1120 and a point 1124. The point 1124 of the mounting screw 1114 may be sufficiently sharp and rigid such that the mounting screw 1114 may be twisted into a sole of a shoe. The threading 1120 may be optimized to ensure the mounting screw 1114 does come un-threaded from the sole of the shoe when a user utilizes the shoe. Additionally, the threading 1120 of the mounting screw 1114 may be optimized such that the mounting screw 1114 may be easily threaded into a sole of a shoe without utilizing a power tool.

As shown in FIGS. 11B and 11C, the screw head 1106 may include a keyhole 1124 disposed into a surface of the screw head 1106. The keyhole 1124 may be configured to receive a hex key (may alternatively be referred to as an Allen wrench) to enable a user to better grasp the screw 1104 to loosen or tighten the screw 1104. The keyhole 1124 enables a user to widen or close a gap formed between the retainer 1112 and a top surface of the head 1116 of the mounting screw 1114.

In an example use-case, a user installs the fastener in a shoe (see, e.g., 1002 at FIGS. 10A-10B) by screwing the mounting screw 1114 into a sole of the shoe. The user may then install the spring-loaded screw assembly 1102 into the mounting screw 1114 by screwing the screw 1104 into the cavity 1118. The user may ensure that the spring-loaded screw assembly 1102 is not fully installed or fully tightened, such that a gap remains between the spring-loaded screw assembly 1102 and the mounting screw 1114. The user may then install the orthosis brace (see 100 first discussed in connection with FIG. 1) around a lower portion of a leg. The user may loop the shoe connectors (see 112a, 112b) of the orthosis brace around the fastener 1100 This gap formed between the mounting screw 1114 and the spring-loaded screw assembly 1102. The user may then tighten the screw 1104 of the spring-loaded screw assembly 1102 to "pinch" the shoe connector and ensure the shoe connector does not release from the fastener 1100. When removing the orthosis brace, the user may loosen the screw 1104 of the spring-loaded screw assembly 1102 and then un-loop the shoe connector from the fastener 1100. Alternatively, the user may allow the orthosis brace to remain attached to the fastener 1100 and simply slip a foot out of the shoe.

Figure 12A:
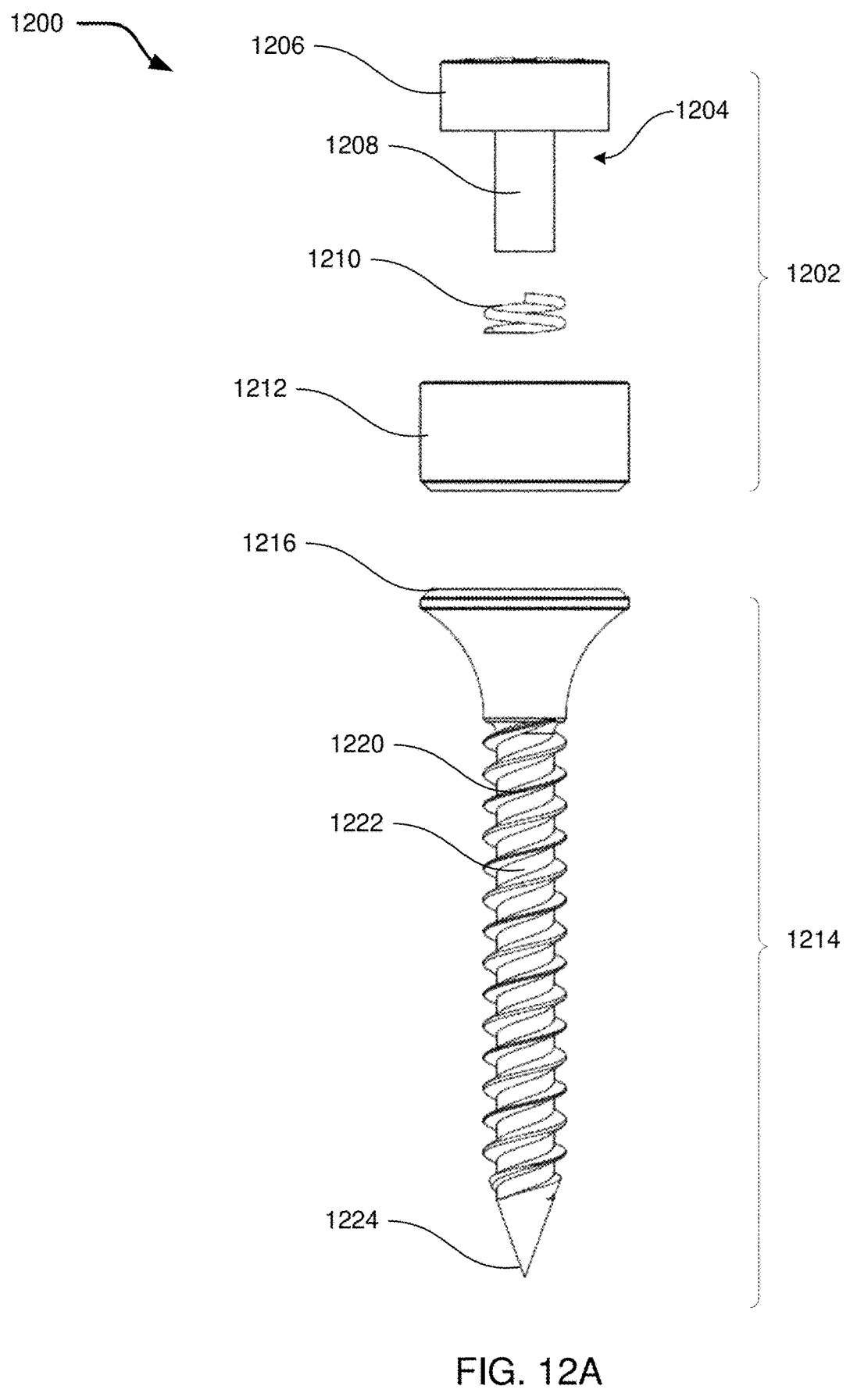
Figure 12B:
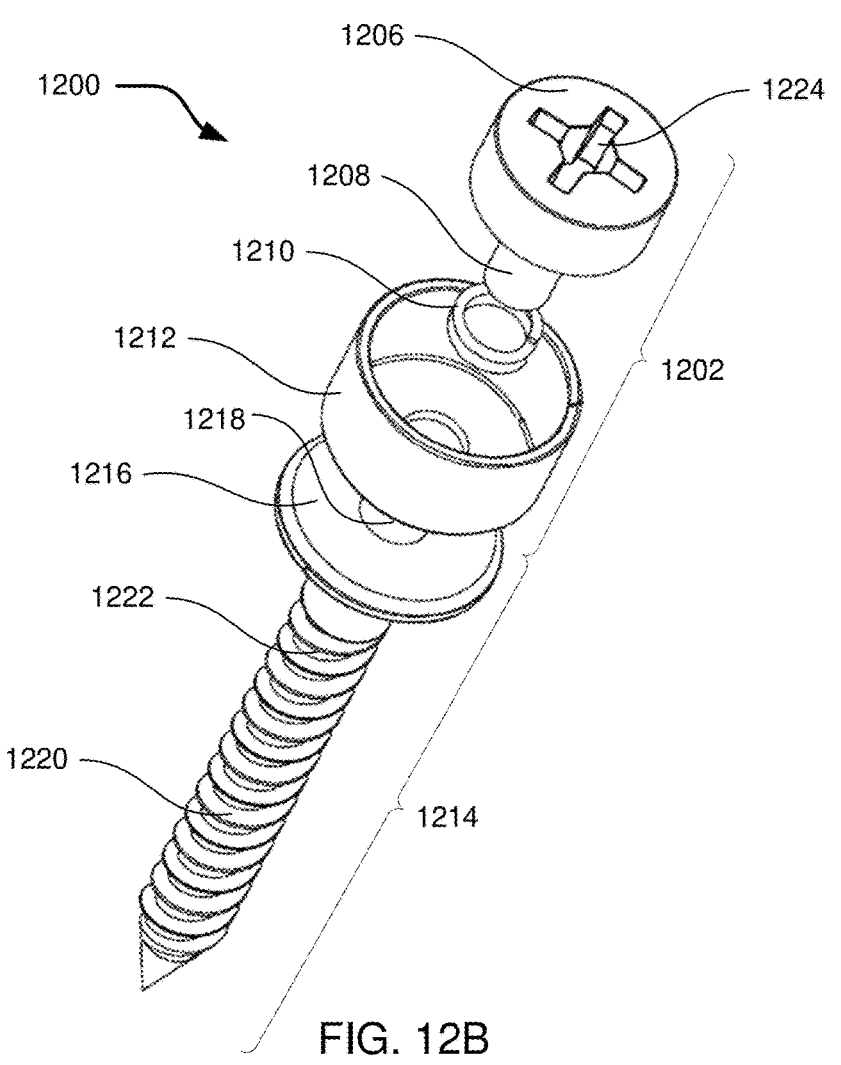
FIG. 12B is an exploded perspective view of an exemplary fastener for releasably coupling an orthosis brace to footwear, such as a shoe.
Figure 12C:
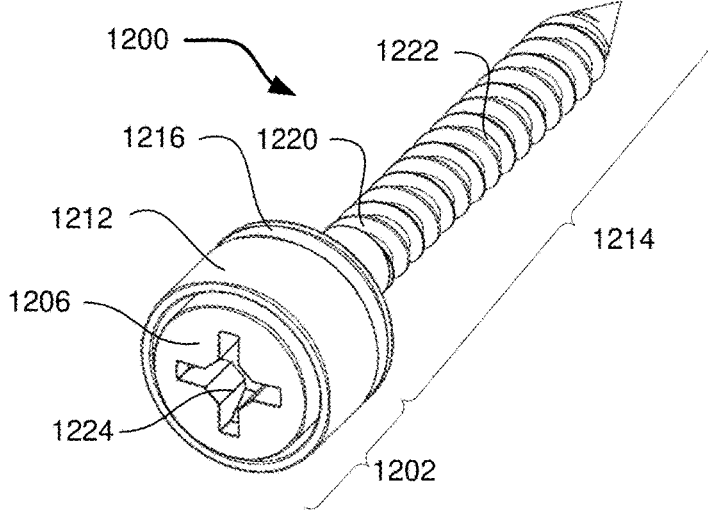
FIG. 12C is a perspective view of an exemplary fastener for releasably coupling an orthosis brace to footwear, such as a shoe.

FIGS. 12A-12C illustrate an example fastener 1200 that may be utilized in connection with the system 1000 illustrated in FIGS. 10A-10B. The example fastener 1200 is similar to the example fastener 1100 discussed in connection with FIGS. 11A-11C. As described herein, the fastener (see 1004a, 1004b at FIGS. 10A-10B) may optionally include a screw or screw assembly as shown in FIGS. 12A-12C. The fastener 1200 illustrated in FIGS. 12A-12C is optimized for insertion into a portion of a shoe and is further optimized to provide a secure head for removably securing the fastener 1200 to the shoe connectors (see 112*a*, 112*b*). FIG. 12A is an exploded straight-on side view of components of the fastener 1200. FIG. 12B is an exploded perspective view of components of the fastener 1200. FIG. 12C is an assembled perspective view of the fastener 1200.

Like the fastener 1100 illustrated in FIGS. 11A-11C, the fastener 1200 includes a spring-loaded screw assembly 1202. The spring-loaded screw assembly 1202 includes a screw 1204, which includes a screw head 1206 and a screw body 1208. The spring-loaded screw assembly 1202 further includes a spring 1210 and a retainer 1212, and the spring 1210 is disposed between the retainer 1212 and the screw head 1206. When the components are assembled, the spring 1210 is disposed around the screw body 1208, and the screw body 1208 is disposed within a hollow interior defined by the retainer 1212. Thus, the spring 1210 and screw body 1208 are disposed within the retainer 1212, and the spring 1210 rests on an interior shoulder of the retainer 1212.

The fastener 1200 further includes a mounting screw 1214. The mounting screw 1214 is configured to be attached to the shoe itself (see, e.g., shoe 1002 at FIGS. 10A-10B). The mounting screw 1214 may be threaded into a sole of the shoe near the toe region of the shoe. The mounting screw 1214 includes a head 1216 and a cavity 1218 cut into the head 1216. The cavity 1218 of the mounting screw 1214 is configured to accept the screw body 1208 of the spring-loaded screw assembly 1202. The mounting screw 1214 further includes a body 1222 that includes threading 1220 and a point 1224. The point 1224 of the mounting screw 1214 may be sufficiently sharp and rigid such that the mounting screw 1214 may be twisted into a sole of a shoe. The threading 1220 may be optimized to ensure the mounting screw 1214 does come un-threaded from the sole of the shoe when a user utilizes the shoe. Additionally, the threading 1220 of the mounting screw 1214 may be optimized such that the mounting screw 1214 may be easily threaded into a sole of a shoe without utilizing a power tool. As shown in FIGS. 12B-12C, the fastener 1200 further includes a keyhole 1224 to enable a user to tighten or loosen the screw 1204 of the spring-loaded screw assembly 1202 into the cavity 1218 of the mounting screw 1214.

Figure 13A:
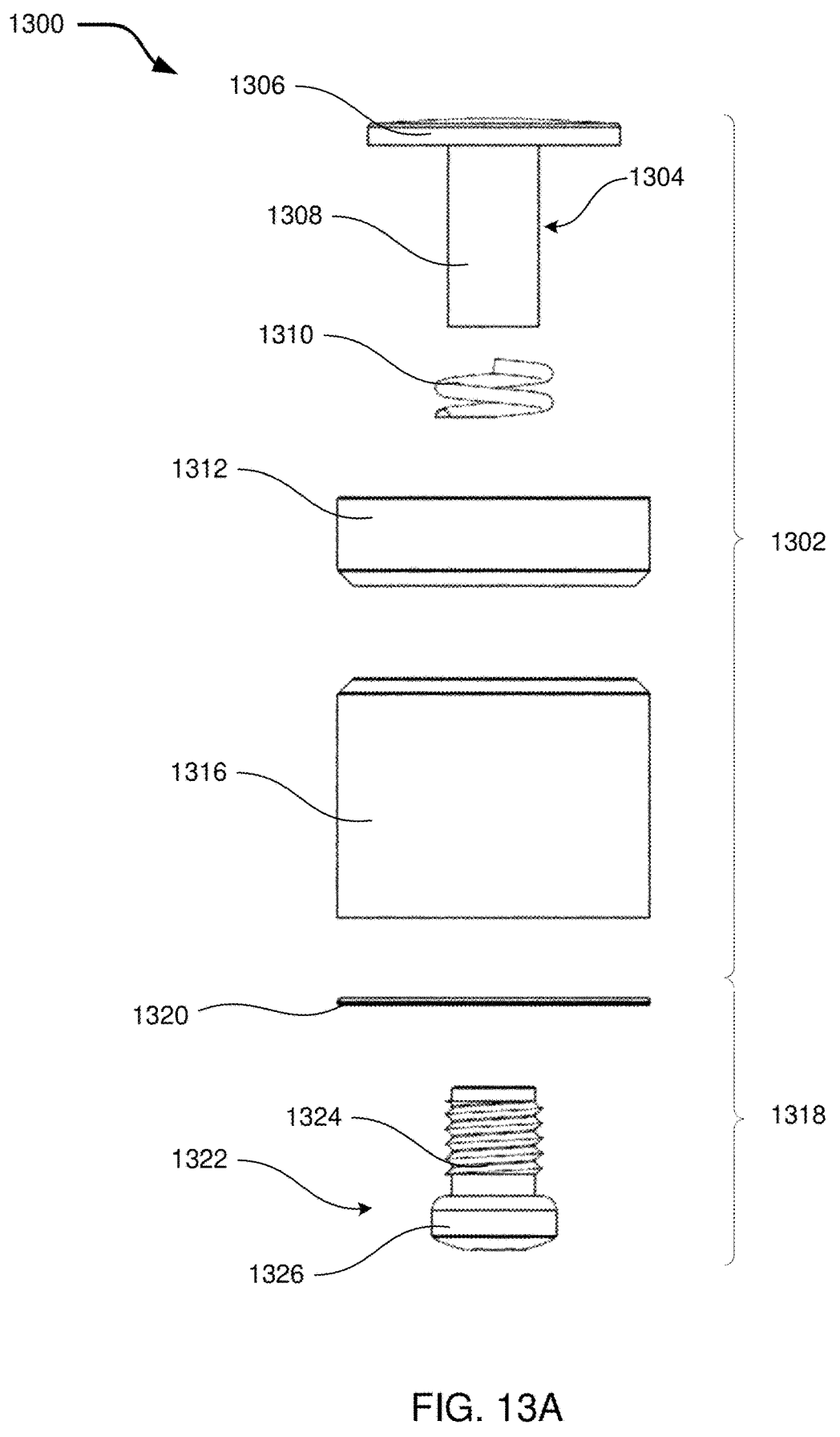
Figures 13B, 13C:
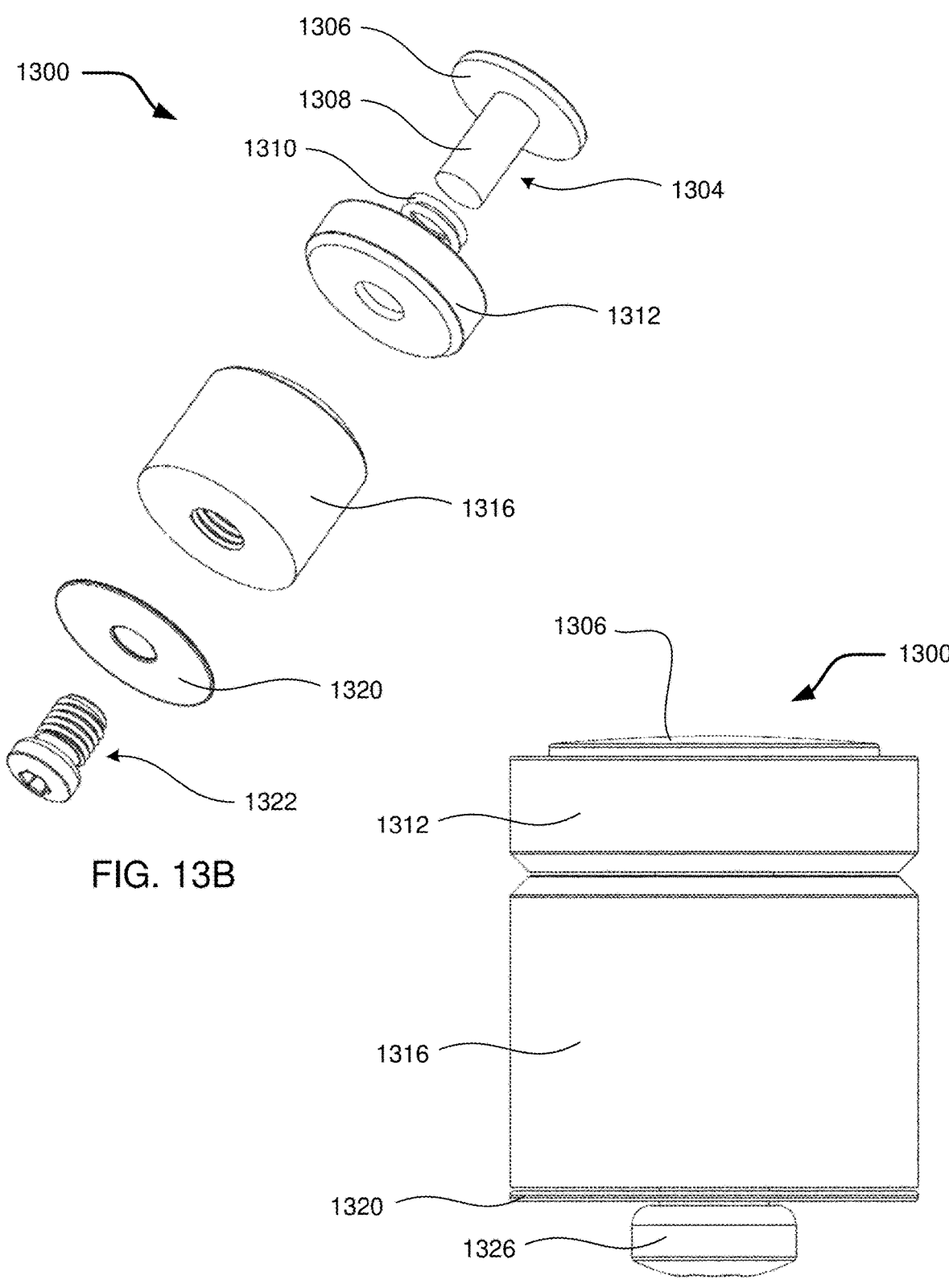
FIG. 13B is an exploded perspective view of an exemplary fastener for releasably coupling an orthosis brace to footwear, such as a shoe.
FIG. 13C is a straight-on side view of an exemplary fastener for releasably coupling an orthosis brace to footwear, such as a shoe.

FIGS. 13A-13C illustrate an example fastener 1300 that may be utilized in connection with the system 1000 illustrated in FIGS. 10A-10B. As described herein, the fastener (see 1004*a*, 1004*b* at FIGS. 10A-10B) may optionally include a screw or screw assembly as shown in FIGS. 13A-13C. The fastener 1300 illustrated in FIGS. 13A-13C is optimized for insertion into a portion of a shoe and is further optimized to provide a secure head for removably securing the fastener 1300 to the shoe connectors (see 112*a*, 112*b*). FIG. 13A is an exploded straight-on side view of components of the fastener 1300. FIG. 13B is an exploded perspective view of components of the fastener 1300. FIG. 13C is an assembled straight-on side view of the fastener 1300.

The fastener 1300 includes an exterior portion 1302 that is configured to be located at an exterior portion of a shoe when the fastener 1300 is installed. The fastener 1300 includes an interior portion 1318 that is configured to be located at an interior portion of the shoe when the fastener is installed. The interior portion 1302 includes a spring-loaded screw assembly that includes a screw 1304 comprising a screw head 1306 and a screw body 1308. The spring-loaded screw assembly additionally includes a spring 1310 and a retainer 1312. The exterior portion 1302 additionally includes a spacer 1316 that comprises a hollow interior comprising threaded walls. The fastener 1300 further includes a mounting screw 1322 that includes a head 1326 and a body that comprises threading 1324. The threaded interior walls of the spacer 1316 are configured to receive the threading 1324 of the mounting screw 1322. The interior portion 1318 additionally includes a washer 1320 configured to be disposed against an interior surface of the shoe when the fastener 1300 is installed.

Figure 14A:
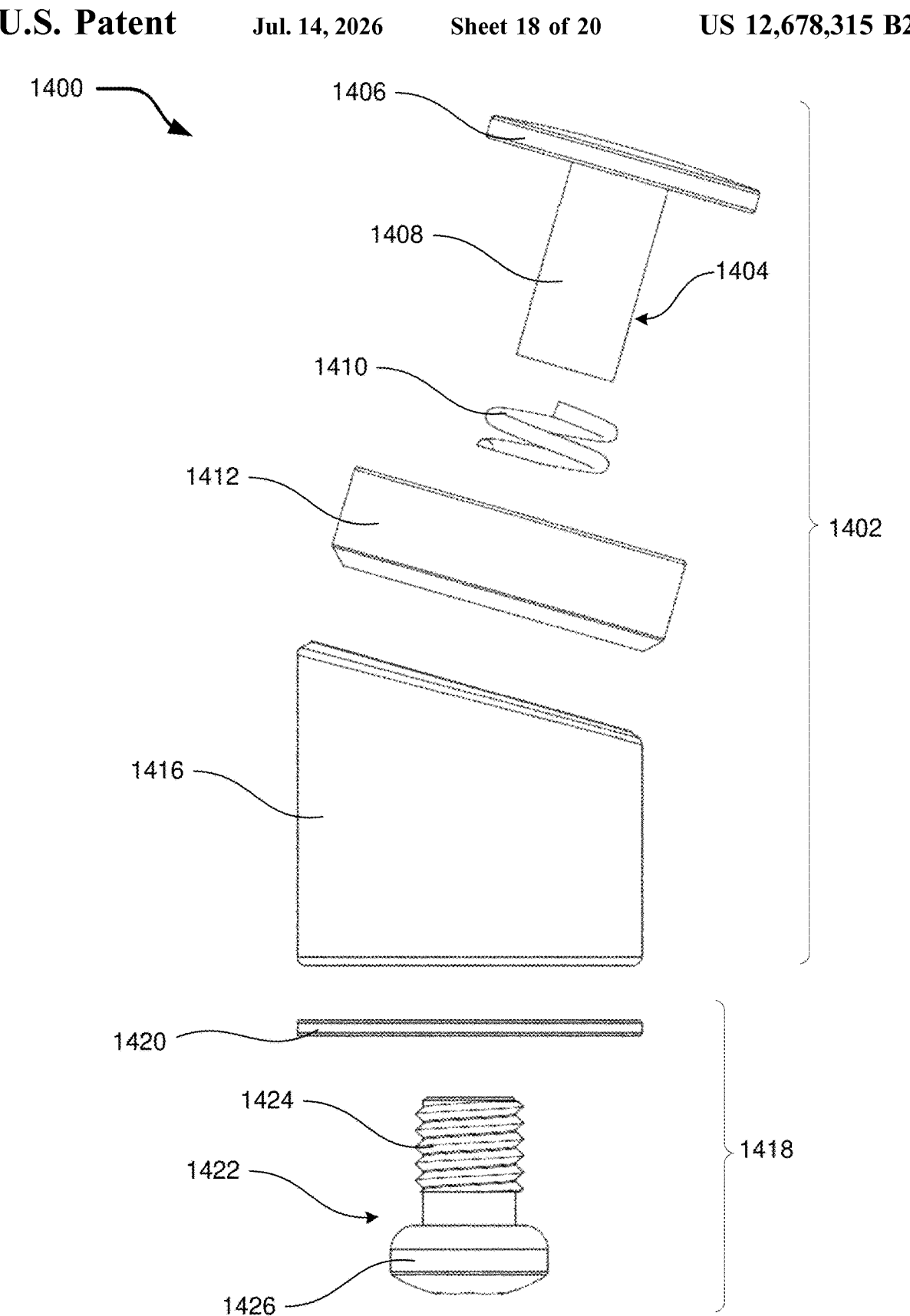
FIG. 14A is an exploded straight-on side view of an exemplary fastener for releasably coupling an orthosis brace to footwear, such as a shoe.
Figure 14B:
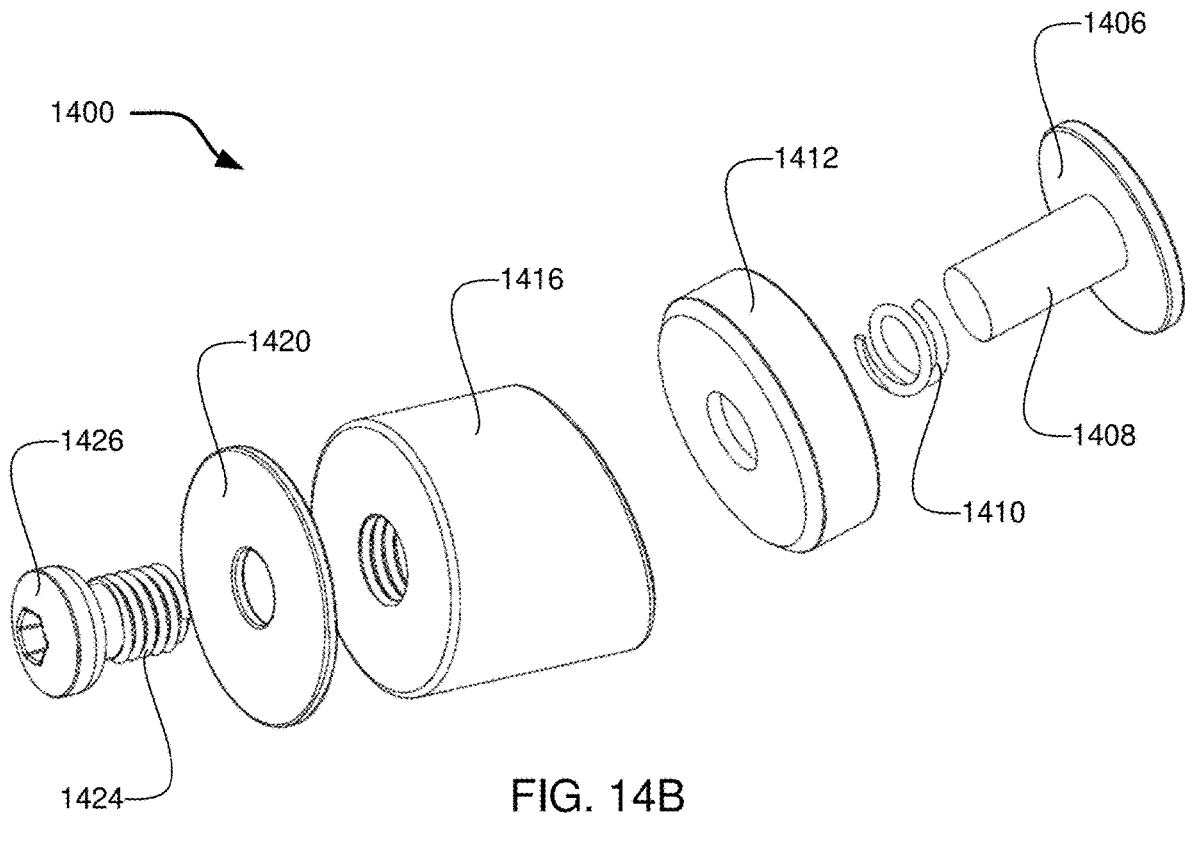
FIG. 14B is an exploded perspective view of an exemplary fastener for releasably coupling an orthosis brace to footwear, such as a shoe.
Figure 14C:
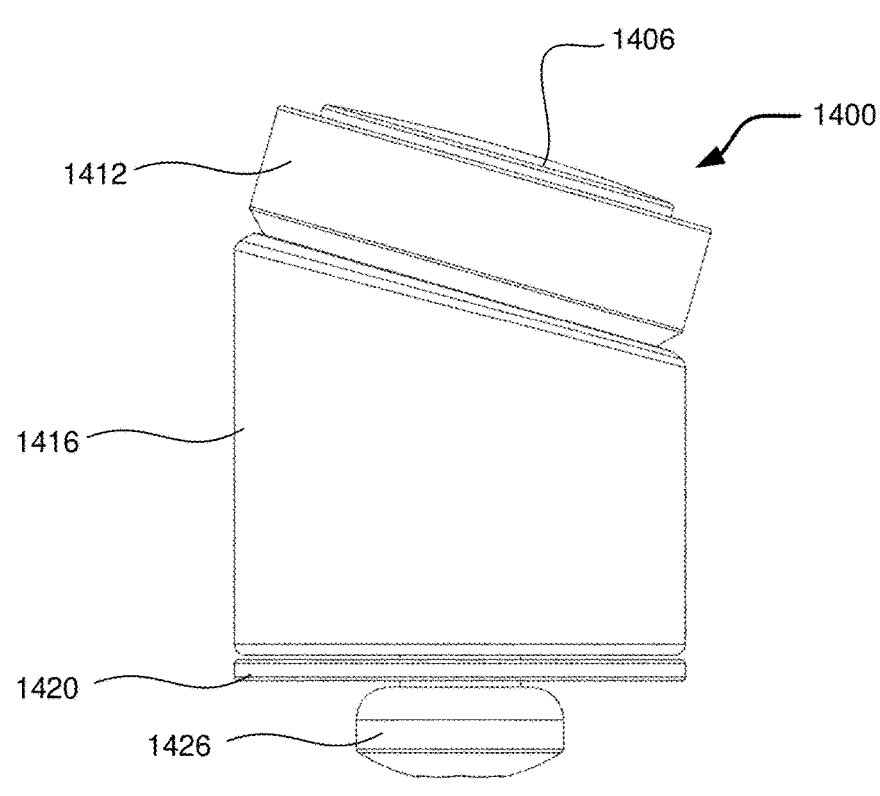
FIG. 14C is a straight-on side view of an exemplary fastener for releasably coupling an orthosis brace to footwear, such as a shoe.

FIGS. 14A-14C illustrate an example fastener 1400 that may be utilized in connection with the system 1000 illustrated in FIGS. 10A-10B. As described herein, the fastener (see 1004*a*, 1004*b* at FIGS. 10A-10B) may optionally include a screw or screw assembly as shown in FIGS. 14A-14C. The fastener 1400 illustrated in FIGS. 14A-14C is optimized for insertion into a portion of a shoe and is further optimized to provide a secure head for removably securing the fastener 1400 to the shoe connectors (see 112*a*, 112*b*). FIG. 14A is an exploded straight-on side view of components of the fastener 1400. FIG. 14B is an exploded perspective view of components of the fastener 1400. FIG. 14C is an assembled straight-on side view of the fastener 1400.

Like the fastener 1300 described in connection with FIGS. 13A-13C, the fastener 1400 includes an exterior portion 1402 that is configured to be located at an exterior portion of a shoe when the fastener 1400 is installed. The fastener 1400 includes an interior portion 1418 that is configured to be located at an interior portion of the shoe when the fastener is installed. The interior portion 1402 includes a spring-loaded screw assembly that includes a screw 1404 comprising a screw head 1406 and a screw body 1408. The spring-loaded screw assembly additionally includes a spring 1410 and a retainer 1412. The exterior portion 1402 additionally includes a spacer 1416 that comprises a hollow interior comprising threaded walls. The fastener 1400 further includes a mounting screw 1422 that includes a head 1426 and a body that comprises threading 1424. The threaded interior walls of the spacer 1416 are configured to receive the threading 1424 of the mounting screw 1422. The interior portion 1418 additionally includes a washer 1420 configured to be disposed against an interior surface of the shoe when the fastener 1400 is installed.

The fastener 1400 illustrated in FIGS. 14A-14C differs from the fastener 1300 illustrated in FIGS. 13A-13C at least because the spacer 1416 of the fastener 1400 comprises an oblique cylindrical geometry. This differs from the right cylindrical geometry of the spacer 1316 illustrated in the fastener 1300 of FIGS. 13A-13C. The oblique cylindrical geometry of the spacer 1416 enables a user to tilt the fastener 1400 back toward the posterior end of the foot. This may enable the user to secure the orthosis brace more easily to the fastener 1400.

Figure 15:
FIG. 15 is a perspective view of a system for releasably coupling an orthosis brace to footwear, such as a shoe, by installing two or more fasteners into the shoe and coupling the orthosis brace to the two or more fasteners, and specifically illustrates wherein the shoe is coupled to the orthosis brace.

FIG. 15 is a perspective view of a system 1500 for releasably coupling an orthosis brace 1504 to footwear, such as a shoe, by installing two or more fasteners into the shoe and coupling the orthosis brace 1504 to the two or more fasteners. The system 1500 is similar to the system 1000 first discussed in connection with FIGS. 10A-10B but illustrates an alternative embodiment with a different form of orthosis brace 1504. The orthosis brace may include any suitable orthosis brace known in the art, including, for example, the orthosis brace 100 first described in connection with FIG. 1, or the orthosis brace 1504 illustrated in FIG. 15. The orthosis brace may specifically include any of the component or features described in connection with the orthosis described in European Patent Specification EP 2 783 661 B1, published Jan. 11, 2017, which is incorporated herein by reference in its entirety.

The orthosis brace 1504 includes a support 1506 that is configured to be disposed around an ankle of a user. The orthosis brace 1504 additionally includes one or more lace supports 1508, which may specifically include a tab, loop, eyelet, hole, or other opening for receiving a lace and holding the lace in place. The orthosis brace 1504 may specifically include three lace supports 1508 as shown in FIG. 15. The orthosis brace 1504 includes a first shoe connector 1512a and a second shoe connector 1512b, which specifically include a first end of a lace and a second end of a lace as shown in FIG. 15. Thus, in some cases, the first shoe connector 1512a and the second shoe connector 1512b are components of a singular item, such as a singular lace coupled to the orthosis brace 1504. The first shoe connector 1512a couples to a lace support 1508 and the first fastener 1004a. The second shoe connector 1512b couples to a lace support 1508 and the second fastener 1004b. As shown in FIG. 15, the lace (forming the first and second shoe connectors 1512a, 1512b) may additionally be fed through another lace support 1508 located in a middle of an anterior side of the orthosis brace 1504. In this implementation, the lace may be wound back and forth to form a "W" or "M" shape as shown in FIG. 15.

EXAMPLES

The following examples pertain to further embodiments.

Example 1 is a device. The device includes a support configured to wrap around at least a portion of a lower leg of a user. The device includes a lace support attached to the support and configured to receive a lace. The device includes a reel-based fastener attached to the support, wherein the reel-based fastener comprises a reel for receiving the lace and adjusting a tautness of the lace.

Example 2 is a device as in Example 1, wherein the support comprises an ankle support portion configured to wrap around a posterior side of the lower leg of the user at or near an ankle of the user.

Example 3 is a device as in any of Examples 1-2, wherein the support further comprises a counter support portion attached to the ankle support portion, wherein the counter support portion is distal relative to the ankle support portion when the device is secured to the lower leg of the user.

Example 4 is a device as in any of Examples 1-3, wherein the counter support portion extends outward relative to the lower leg of the user when the device is secured to the lower leg of the user such that the counter support portion provides sufficient space for a counter of the user's footwear.

Example 5 is a device as in any of Examples 1-4, wherein the lace comprises a single line comprising a first end and a second end, and wherein each of the first end and the second end of the lace is attached to the reel-based fastener.

Example 6 is a device as in any of Examples 1-5, wherein the reel-based fastener is configured to be rotated by a user, and wherein rotating the reel-based fastener causes the lace to one or more of: wind on to the reel and increase the tautness of the lace; or unwind from the reel and decrease the tautness of the lace.

Example 7 is a device as in any of Examples 1-6, wherein the lace support comprises a plurality of lace supports for receiving and securing the lace to the device.

Example 8 is a device as in any of Examples 1-7, wherein: the lace comprises a first shoe connector and a second shoe connector; each of the first shoe connector and the second shoe connector comprises a shoe fastener for securing the device to a footwear of the user; and the shoe fastener comprises one or more of a loop formed by the lace, a hook, a snap, a knot, a button, or a latch.

Example 9 is a device as in any of Examples 1-8, wherein the support comprises a counter support portion, and wherein the counter support portion comprises a footwear counter brace configured to brace against a counter of the user's footwear, wherein the footwear counter brace comprises a curvature approximately inverse to a curvature of the counter of the user's footwear.

Example 10 is a device as in any of Examples 1-9, wherein the support comprises a first support edge and a second support edge, and wherein the support is configured to wrap around a posterior portion of the lower leg of the user such that each of the first support edge and the second support edge terminate at an anterior portion of the lower leg of the user.

Example 11 is a device as in any of Examples 1-10, wherein the first support edge does not come in contact with the second support edge when the device is worn by the user such that the support wraps around a posterior portion of the lower leg of the user and provides an open space at the anterior portion of the lower leg of the user.

Example 12 is a device as in any of Examples 1-11, wherein the lace support comprises a plurality of loops configured for releasably receiving the lace, wherein the plurality of loops comprise one or more of: a first loop located near the first support edge; a second loop located near the first support edge; a first loop located near the second support edge; a second loop located near the second support edge; and a posterior loop located near the reel-based fastener on a posterior side of the device, wherein the posterior side of the device is located at a posterior side of the user when the device is worn by the user.

Example 13 is a device as in any of Examples 1-12, wherein: the lace is threaded through the first loop located near the first support edge and the second loop located near the first support edge such that the lace forms a first shoe connector loop at the first support edge; and the lace is threaded through the first loop located near the second support edge and the second loop located near the second support edge such that the lace forms a second shoe connector loop at the second support edge.

Example 14 is a device as in any of Examples 1-13, wherein each of the first shoe connector loop and the second shoe connector loop is configured to releasably secure the device to a shoe worn by the user.

Example 15 is a device as in any of Examples 1-14, wherein the support comprises a rigid inner frame and an outer padding, wherein the rigid inner frame comprises a curvature approximately matching an outer curvature of the lower leg of the user.

Example 16 is a device as in any of Examples 1-15, wherein the lace support comprises four or more lace supports attached to the support, and wherein each of the four or more lace supports comprises a loop configured for releasably receiving the lace therein.

Example 17 is a device as in any of Examples 1-16, wherein the device is configured to alleviate foot drop experienced by the user.

Example 18 is a device as in any of Examples 1-17, wherein the support comprises sufficient rigidity to resist collapsing when the device is worn by the user and the user is walking.

Example 19 is a device as in any of Examples 1-18, wherein: the tautness of the lace is increased or decreased by the reel-based fastener when the support is wrapped around the lower leg of the user and the lace is secured to a shoe worn by the user; the reel-based fastener is configured to increase the tautness of the lace when the reel is rotated in a clockwise direction; and the reel-based fastener is config-ured to decrease the tautness of the lace when the reel is rotated in a counter-clockwise direction.

Example 20 is a device as in any of Examples 1-19, wherein the reel-based fastener comprises a locking mecha-nism for locking the reel and preventing the lace from unwinding from the reel.

Example 21 is a system. The system includes a shoe comprising shoe counter. The system includes a support configured to wrap around at least a portion of a lower leg of a user. The system includes a lace support attached to the support and configured to receive a lace. The system includes a reel-based fastener attached to the support, wherein the reel-based fastener comprises a reel for receiv-ing the lace and adjusting a tautness of the lace.

Example 22 is a system as in Example 21, wherein the support comprises an ankle support portion configured to wrap around a posterior side of the lower leg of the user at or near an ankle of the user.

Example 23 is a system as in any of Examples 21-22, wherein the support further comprises a counter support portion attached to the ankle support portion, wherein the counter support portion is distal relative to the ankle support portion when the device is secured to the lower leg of the user.

Example 24 is a system as in any of Examples 21-23, wherein the counter support portion extends outward rela-tive to the lower leg of the user when the device is secured to the lower leg of the user such that the counter support portion provides sufficient space for the shoe counter of the shoe.

Example 25 is a system as in any of Examples 21-24, wherein the lace comprises a single line comprising a first end and a second end, and wherein each of the first end and the second end of the lace is attached to the reel-based fastener.

Example 26 is a system as in any of Examples 21-25, wherein the reel-based fastener is configured to be rotated by a user, and wherein rotating the reel-based fastener causes the lace to one or more of: wind on to the reel and increase the tautness of the lace; or unwind from the reel and decrease the tautness of the lace.

Example 27 is a system as in any of Examples 21-26, wherein the lace support comprises a plurality of lace supports for receiving and securing the lace to the device.

Example 28 is a system as in any of Examples 21-27, wherein: the lace comprises a first shoe connector and a second shoe connector; each of the first shoe connector and the second shoe connector comprises a shoe fastener for securing the device to a footwear of the user; and the shoe fastener comprises one or more of a loop formed by the lace, a hook, a snap, a knot, a button, or a latch.

Example 29 is a system as in any of Examples 21-28, wherein the support comprises a counter support portion, and wherein the counter support portion comprises a foot-wear counter brace configured to brace against the shoe counter of the shoe, wherein the footwear counter brace comprises a curvature approximately inverse to a curvature of the shoe counter of the shoe.

Example 30 is a system as in any of Examples 21-29, wherein the support comprises a first support edge and a second support edge, and wherein the support is configured to wrap around a posterior portion of the lower leg of the user such that each of the first support edge and the second support edge terminate at an anterior portion of the lower leg of the user.

Example 31 is a system as in any of Examples 21-30, wherein the first support edge does not come in contact with the second support edge when the device is worn by the user such that the support wraps around a posterior portion of the lower leg of the user and provides an open space at the anterior portion of the lower leg of the user.

Example 32 is a system as in any of Examples 21-31, wherein the lace support comprises a plurality of loops configured for releasably receiving the lace, wherein the plurality of loops comprise one or more of: a first loop located near the first support edge; a second loop located near the first support edge; a first loop located near the second support edge; a second loop located near the second support edge; and a posterior loop located near the reel-based fastener on a posterior side of the device, wherein the posterior side of the device is located at a posterior side of the user when the device is worn by the user.

Example 33 is a system as in any of Examples 21-32, wherein: the lace is threaded through the first loop located near the first support edge and the second loop located near the first support edge such that the lace forms a first shoe connector loop at the first support edge; and the lace is threaded through the first loop located near the second support edge and the second loop located near the second support edge such that the lace forms a second shoe con-nector loop at the second support edge.

Example 34 is a system as in any of Examples 21-33, wherein each of the first shoe connector loop and the second shoe connector loop is configured to releasably secure the device to a shoe worn by the user.

Example 35 is a system as in any of Examples 21-34, wherein the support comprises a rigid inner frame and an outer padding, wherein the rigid inner frame comprises a curvature approximately matching an outer curvature of the lower leg of the user.

Example 36 is a system as in any of Examples 21-35, wherein the lace support comprises four or more lace supports attached to the support, and wherein each of the four or more lace supports comprises a loop configured for releasably receiving the lace therein.

Example 37 is a system as in any of Examples 21-36, wherein the device is configured to alleviate foot drop experienced by the user.

Example 38 is a system as in any of Examples 21-37, wherein the support comprises sufficient rigidity to resist collapsing when the device is worn by the user and the user is walking.

Example 39 is a system as in any of Examples 21-38, wherein: the tautness of the lace is increased or decreased by the reel-based fastener when the support is wrapped around the lower leg of the user and the lace is secured to a shoe worn by the user; the reel-based fastener is configured to increase the tautness of the lace when the reel is rotated in a clockwise direction; and the reel-based fastener is config-ured to decrease the tautness of the lace when the reel is rotated in a counter-clockwise direction.

Example 40 is a system as in any of Examples 21-39, wherein the reel-based fastener comprises a locking mecha-nism for locking the reel and preventing the lace from unwinding from the reel.

Example 41 is a system. The system includes a first fastener configured to attach to a shoe and a second fastener configured to attach to the shoe. The system includes a support configured to wrap around at least a portion of a lower leg of a user. The system includes a lace support attached to the support, wherein the lace support is configured to receive a lace, and wherein the lace forms a first shoe connector and a second shoe connector. Thes system is such that the first shoe connector is configured to be coupled to the first fastener to releasably couple the support to the shoe when the first fastener is attached to the shoe. The system is such that the second shoe connector is configured to be coupled to the second fastener to releasably couple the support to the shoe when the second fastener is attached to the shoe.

Example 42 is a system as in Example 41, wherein the first shoe connector comprises a first loop formed by a first portion of the lace; wherein the first fastener comprises a first head and a first body; wherein the first loop is disposed around the first body of the first fastener; and wherein at least a portion of the first portion of the lace runs along a medial side of the shoe when the support is coupled to the shoe.

Example 43 is a system as in any of Examples 41-42, wherein the second shoe connector comprises a second loop formed by a second portion of the lace; wherein the second fastener comprises a second head and a second body; wherein the second loop is disposed around the second body of the second fastener; and wherein at least a portion of the second portion of the lace runs along a lateral side of the shoe when the support is coupled to the shoe.

Example 44 is a system as in any of Examples 41-43, wherein the first fastener is configured to be attached to a sole of the shoe at a medial side of the shoe; and wherein the second fastener is configured to be attached to the sole of the shoe at a lateral side of the shoe.

Example 45 is a system as in any of Examples 41-44, wherein each of the first fastener and the second fastener comprises a spring-loaded screw assembly that comprises: a screw comprising a screw head and a screw body; a spring; and a retainer.

Example 46 is a system as in any of Examples 41-45, further comprising a spacer, wherein the spacer comprises a right cylindrical geometry.

Example 47 is a system as in any of Examples 41-46, further comprising a spacer, wherein the spacer comprises an oblique cylindrical geometry.

Example 48 is a system as in any of Examples 41-47, wherein the spring is disposed around the screw body; wherein the retainer comprises a hollow interior space defined by a cylindrical sidewall; and wherein each of the spring and the screw body is disposed within the hollow interior space of the retainer.

Example 49 is a system as in any of Examples 41-48, wherein the first shoe connector comprises a first loop that is looped around the screw body of the first fastener and is disposed in between the retainer and the screw head of the first fastener; and wherein the second shoe connector comprises a second loop that is looped around the screw body of the second fastener and is disposed in between the retainer and the screw head of the second fastener.

Example 50 is a system as in any of Examples 41-49, wherein each of the first fastener and the second fastener further comprises a mounting screw.

Example 51 is a system as in any of Examples 41-50, wherein the mounting screw of the first fastener comprises first threading that is configured to be threaded into a sole of the shoe at a medial side of the shoe; and wherein the mounting screw of the second fastener comprises second threading that is configured to be threaded into the sole of the shoe at a lateral side of the shoe.

Example 52 is a system as in any of Examples 41-51, wherein, for each of the first fastener and the second fastener: the mounting screw comprises a mounting cavity disposed within a head of the mounting screw; and the screw body of the screw is configured to be threaded into the mounting cavity to couple the screw to the mounting screw.

Example 53 is a system as in any of Examples 41-52, wherein at least one of the first fastener or the second fastener comprises a hook.

Example 54 is a system as in any of Examples 41-53, wherein the support comprises an ankle support portion configured to wrap around a posterior side of the lower leg of the user at or near an ankle of the user; wherein the support further comprises a counter support portion attached to the ankle support portion, wherein the counter support portion is distal relative to the ankle support portion when the system is secured to the lower leg of the user; and wherein the counter support portion extends outward relative to the lower leg of the user when the system is secured to the lower leg of the user such that the counter support portion provides sufficient space for a counter of the user's footwear.

Example 55 is a system as in any of Examples 41-54, wherein the system includes a reel-based fastener attached to the support, wherein the reel-based fastener comprises a reel for receiving the lace and adjusting a tautness of the lace, and wherein the lace comprises a single line comprising a first end and a second end, and wherein each of the first end and the second end of the lace is attached to the reel-based fastener.

Example 56 is a system as in any of Examples 41-55, wherein the reel-based fastener is configured to be rotated by a user, and wherein rotating the reel-based fastener causes the lace to one or more of: wind on to the reel and increase the tautness of the lace; or unwind from the reel and decrease the tautness of the lace.

Example 57 is a system as in any of Examples 41-56, wherein each of the first shoe connector and the second shoe connector comprises a shoe fastener for releasably coupling the support to the shoe; and wherein the shoe fastener comprises one or more of a loop formed by the lace, a hook, a snap, a knot, a button, or a latch.

Example 58 is a system as in any of Examples 41-57, wherein the support comprises a rigid inner frame and an outer padding, wherein the rigid inner frame comprises a curvature approximately matching an outer curvature of the lower leg of the user.

Example 59 is a system as in any of Examples 41-58, wherein the system is configured to alleviate foot drop experienced by the user, and wherein the support comprises sufficient rigidity to resist collapsing when the system is worn by the user and the user is walking.

Example 60 is a system as in any of Examples 41-59, wherein the system includes a reel-based fastener attached to the support, wherein the reel-based fastener comprises a reel for receiving the lace and adjusting a tautness of the lace, and wherein the tautness of the lace is increased or decreased by the reel-based fastener when the support is wrapped around the lower leg of the user and the lace is secured to the shoe when the shoe is worn by the user; wherein the reel-based fastener is configured to increase the tautness of the lace when the reel is rotated in a clockwise direction; wherein the reel-based fastener is configured to decrease the tautness of the lace when the reel is rotated in a counterclockwise direction; and wherein the reel-based fastener comprises a locking mechanism for locking the reel and preventing the lace from unwinding from the reel.

Example 61 is a system as in any of Examples 41-60, wherein one or more of the first fastener or the second fastener is a carabiner.

Example 62 is a system as in any of Examples 41-61, wherein one or more of the first fastener or the second fastener is a loop.

Example 63 is a system as in any of Examples 41-62, wherein one or more of the first fastener or the second fastener is a hook.

Example 64 is a system as in any of Examples 41-63, wherein each of the first fastener and the second fastener is a means for securing the orthosis brace to the shoe.

Example 65 is a system as in any of Examples 41-64, wherein at least one of the first shoe connector and the second shoe connector comprises a fastening element attached to the lace, and wherein the fastening element comprises one or more of a snap, knot, hook, button, or latch.

Example 66 is a system as in any of Examples 41-65, wherein the system includes any of the components of any of Examples 1-40.

In the above disclosure, reference has been made to the accompanying drawings, which form a part hereof, and in which is shown by way of illustration specific implementations in which the disclosure may be practiced. It is understood that other implementations may be utilized, and structural changes may be made without departing from the scope of the present disclosure. References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

While various embodiments of the present disclosure have been described above, it should be understood that they have been presented by way of example only, and not limitation. It will be apparent to persons skilled in the relevant art that various changes in form and detail can be made therein without departing from the spirit and scope of the disclosure. Thus, the breadth and scope of the present disclosure should not be limited by any of the above-described exemplary embodiments but should be defined only in accordance with the following claims and their equivalents. The foregoing description has been presented for the purposes of illustration and description. It is not intended to be exhaustive or to limit the disclosure to the precise form disclosed. Many modifications and variations are possible in light of the above teaching. Further, it should be noted that any or all of the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. A system comprising:
a first fastener configured to attach to a shoe;
a second fastener configured to attach to the shoe;
a support configured to wrap around at least a portion of a lower leg of a user;
a lace support attached to the support, wherein the lace support is configured to receive a lace;
a first shoe connector that is configured to be coupled to the first fastener to releasably couple the support to the shoe when the first fastener is attached to the shoe; and
a second shoe connector that is configured to be coupled to the second fastener to releasably couple the support to the shoe when the second fastener is attached to the shoe; wherein each of the first fastener and the second fastener comprises a spring-loaded screw assembly that comprises:
a screw comprising a screw head and a screw body;
a spring; and
a retainer;
wherein each of the first fastener and the second fastener further comprises a mounting screw;
wherein, for each of the first fastener and the second fastener:
the mounting screw comprises a mounting cavity disposed within a head of the mounting screw; and
the screw body of the screw is configured to be threaded into the mounting cavity to couple the screw to the mounting screw.

2. The system of claim 1, wherein the first shoe connector comprises a first loop formed by a first portion of the lace;
wherein the first fastener comprises a first head and a first body;
wherein the first loop is disposed around the first body of the first fastener; and
wherein at least a portion of the first portion of the lace runs along a medial side of the shoe when the support is coupled to the shoe.

3. The system of claim 2, wherein the second shoe connector comprises a second loop formed by a second portion of the lace;
wherein the second fastener comprises a second head and a second body;
wherein the second loop is disposed around the second body of the second fastener; and
wherein at least a portion of the second portion of the lace runs along a lateral side of the shoe when the support is coupled to the shoe.

4. The system of claim 1, wherein the first fastener is configured to be attached to a sole of the shoe at a medial side of the shoe; and
wherein the second fastener is configured to be attached to the sole of the shoe at a lateral side of the shoe.

5. The system of claim 1, further comprising a spacer, wherein the spacer comprises a right cylindrical geometry.

6. The system of claim 1, further comprising a spacer, wherein the spacer comprises an oblique cylindrical geometry.

7. The system of claim 1, wherein the spring is disposed around the screw body;
wherein the retainer comprises a hollow interior space defined by a cylindrical sidewall; and
wherein each of the spring and the screw body is disposed within the hollow interior space of the retainer.

8. The system of claim 7, wherein the first shoe connector comprises a first loop that is looped around the screw body of the first fastener and is disposed in between the retainer and the screw head of the first fastener; and wherein the second shoe connector comprises a second loop that is looped around the screw body of the second fastener and is disposed in between the retainer and the screw head of the second fastener.

9. The system of claim 1, wherein the mounting screw of the first fastener comprises first threading that is configured to be threaded into a sole of the shoe at a medial side of the shoe; and wherein the mounting screw of the second fastener comprises second threading that is configured to be threaded into the sole of the shoe at a lateral side of the shoe.

10. The system of claim 1, wherein at least one of the first fastener or the second fastener comprises one or more of a hook, a loop, a knob, or a carabiner.

11. The system of claim 1, wherein the support comprises an ankle support portion configured to wrap around a posterior side of the lower leg of the user at or near an ankle of the user;

wherein the support further comprises a counter support portion attached to the ankle support portion, wherein the counter support portion is distal relative to the ankle support portion when the system is secured to the lower leg of the user; and wherein the counter support portion extends outward relative to the lower leg of the user when the system is secured to the lower leg of the user such that the counter support portion provides sufficient space for a counter of the user's footwear.

12. The system of claim 1, wherein the system further comprises a reel-based fastener attached to the support, wherein the reel-based fastener comprises a reel for receiving the lace and adjusting a tautness of the lace;

wherein the lace comprises a single line comprising a first end and a second end, and wherein each of the first end and the second end of the lace is attached to the reel-based fastener.

13. The system of claim 12, wherein the reel-based fastener is configured to be rotated by a user, and wherein rotating the reel-based fastener causes the lace to one or more of:

wind on to the reel and increase the tautness of the lace; or unwind from the reel and decrease the tautness of the lace.

14. The system of claim 1, wherein each of the first shoe connector and the second shoe connector comprises a shoe fastener for releasably coupling the support to the shoe; and wherein the shoe fastener comprises one or more of a loop formed by the lace, a hook, a snap, a knot, a button, or a latch.

15. The system of claim 1, wherein the support comprises a rigid inner frame and an outer padding, wherein the rigid inner frame comprises a curvature approximately matching an outer curvature of the lower leg of the user.

16. The system of claim 1, wherein the system is configured to alleviate foot drop experienced by the user, and wherein the support comprises sufficient rigidity to resist collapsing when the system is worn by the user and the user is walking.

17. The system of claim 1, wherein the system further comprises a reel-based fastener attached to the support, wherein the reel-based fastener comprises a reel for receiving the lace and adjusting a tautness of the lace;

wherein the tautness of the lace is increased or decreased by the reel-based fastener when the support is wrapped around the lower leg of the user and the lace is secured to the shoe when the shoe is worn by the user;

wherein the reel-based fastener is configured to increase the tautness of the lace when the reel is rotated in a clockwise direction;

wherein the reel-based fastener is configured to decrease the tautness of the lace when the reel is rotated in a counter-clockwise direction; and wherein the reel-based fastener comprises a locking mechanism for locking the reel and preventing the lace from unwinding from the reel.

18. The system of claim 1, wherein at least one of the first shoe connector and the second shoe connector comprises a fastening element attached to the lace, and wherein the fastening element comprises one or more of a snap, knot, hook, button, or latch.

\* \* \* \* \*